(12) United States Patent
Price

(10) Patent No.: US 9,897,500 B2
(45) Date of Patent: Feb. 20, 2018

(54) METHOD FOR ESTABLISHING THE PRESENCE OF SPECIFIED CHARACTERISTICS OF A CONTAINER PRODUCT AND DEVICE FOR PERFORMING SAID METHOD

(75) Inventor: Jeffrey L. Price, Windermere, FL (US)

(73) Assignee: KOCHER-PLASTIK MASCHINENBAU GMBH, Sulzbach-Laufen (DE)

(*) Notice: Subject to any disclaimer, the term of this patent is extended or adjusted under 35 U.S.C. 154(b) by 625 days.

(21) Appl. No.: 13/261,825

(22) PCT Filed: Aug. 28, 2012

(86) PCT No.: PCT/EP2012/003612
§ 371 (c)(1),
(2), (4) Date: Apr. 18, 2014

(87) PCT Pub. No.: WO2013/034255
PCT Pub. Date: Mar. 14, 2013

(65) Prior Publication Data
US 2014/0216893 A1    Aug. 7, 2014

Related U.S. Application Data

(60) Provisional application No. 61/531,252, filed on Sep. 6, 2011.

(51) Int. Cl.
*G01L 5/04* (2006.01)
*G01L 5/00* (2006.01)
*B65B 61/04* (2006.01)
*G01N 35/02* (2006.01)
*B65B 3/00* (2006.01)

(52) U.S. Cl.
CPC ............ *G01L 5/0042* (2013.01); *B65B 61/04* (2013.01); *B65B 3/006* (2013.01); *G01N 35/025* (2013.01); *G01N 2203/0025* (2013.01)

(58) Field of Classification Search
CPC ....... B65B 3/006; B65B 61/04; G01L 5/0042; G01N 2203/0025; G01N 35/025
See application file for complete search history.

(56) References Cited

U.S. PATENT DOCUMENTS 3,716,910 A * 2/1973 Eggert .................. B07C 5/3408
                                                        192/125 A
4,674,340 A * 6/1987 Burt ...................... B67B 3/2006
                                                        73/847
4,696,144 A * 9/1987 Bankuty ............... B67B 3/2053
                                                        53/314
(Continued)

FOREIGN PATENT DOCUMENTS

DE    20 2010 015629 U1    4/2011
EP         0 026 828 A1    4/1981
(Continued)

*Primary Examiner* — Natalie Huls
(74) *Attorney, Agent, or Firm* — Wenderoth, Lind & Ponack L.L.P.

(57) ABSTRACT

A method establishes the presence of specified characteristics of a container product (9, 11), more particularly of a plastic material. The value of at least one specified characteristic is automatically recorded and compared with the reference value for that characteristic in at least one testing station (1-7) of a testing device.

22 Claims, 20 Drawing Sheets

(56) References Cited

U.S. PATENT DOCUMENTS

| | | | | | |
|---|---|---|---|---|---|
| 4,751,805 | A | * | 6/1988 | Walter | B29C 51/18 53/168 |
| 4,907,700 | A | * | 3/1990 | Bankuty | B07C 5/34 209/529 |
| 4,912,318 | A | * | 3/1990 | Kajiura | B07C 5/126 209/526 |
| 4,945,714 | A | * | 8/1990 | Bodolay | B65B 9/093 493/194 |
| 7,536,843 | B2 | * | 5/2009 | Djurle | B65B 1/32 141/100 |
| 2004/0163518 | A1 | * | 8/2004 | Resterhouse | B65B 61/04 83/451 |
| 2005/0034580 | A1 | * | 2/2005 | Finetti | B65B 61/065 83/209 |
| 2006/0219609 | A1 | * | 10/2006 | Canepa | B07C 5/3404 209/552 |
| 2010/0307309 | A1 | * | 12/2010 | Hansen | B26D 7/0006 83/613 |
| 2011/0147097 | A1 | * | 6/2011 | Troisi | B67C 3/202 177/145 |
| 2013/0017289 | A1 | * | 1/2013 | Kieburg | B23K 26/38 425/174.4 |
| 2014/0326519 | A1 | * | 11/2014 | Moulder | G01G 15/00 177/145 |

FOREIGN PATENT DOCUMENTS

| | | |
|---|---|---|
| EP | 0 328 249 A1 | 8/1989 |
| EP | 0 328 374 A2 | 8/1989 |
| EP | 2 269 558 A1 | 1/2011 |
| EP | 2 392 516 A1 | 5/2011 |

* cited by examiner

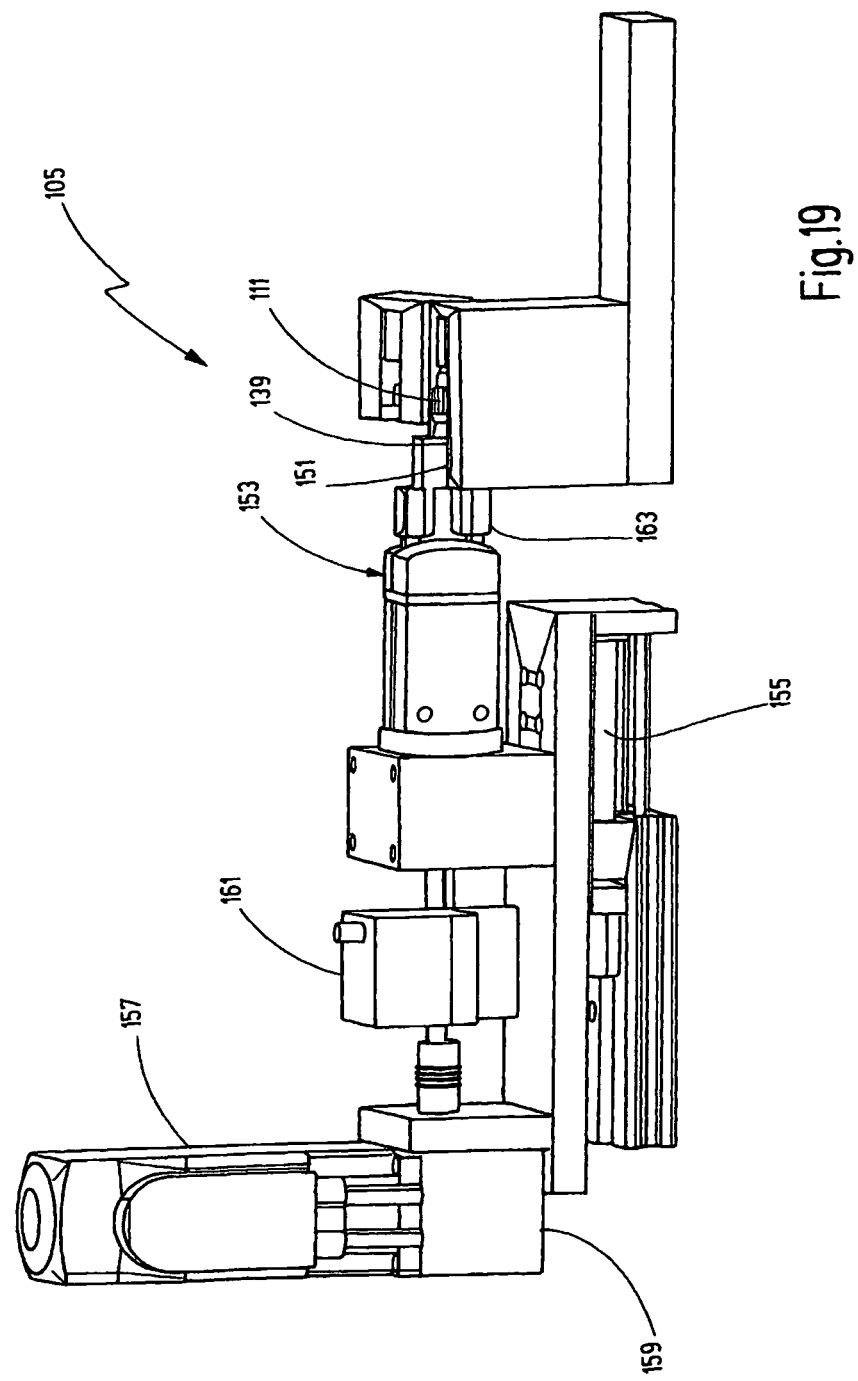

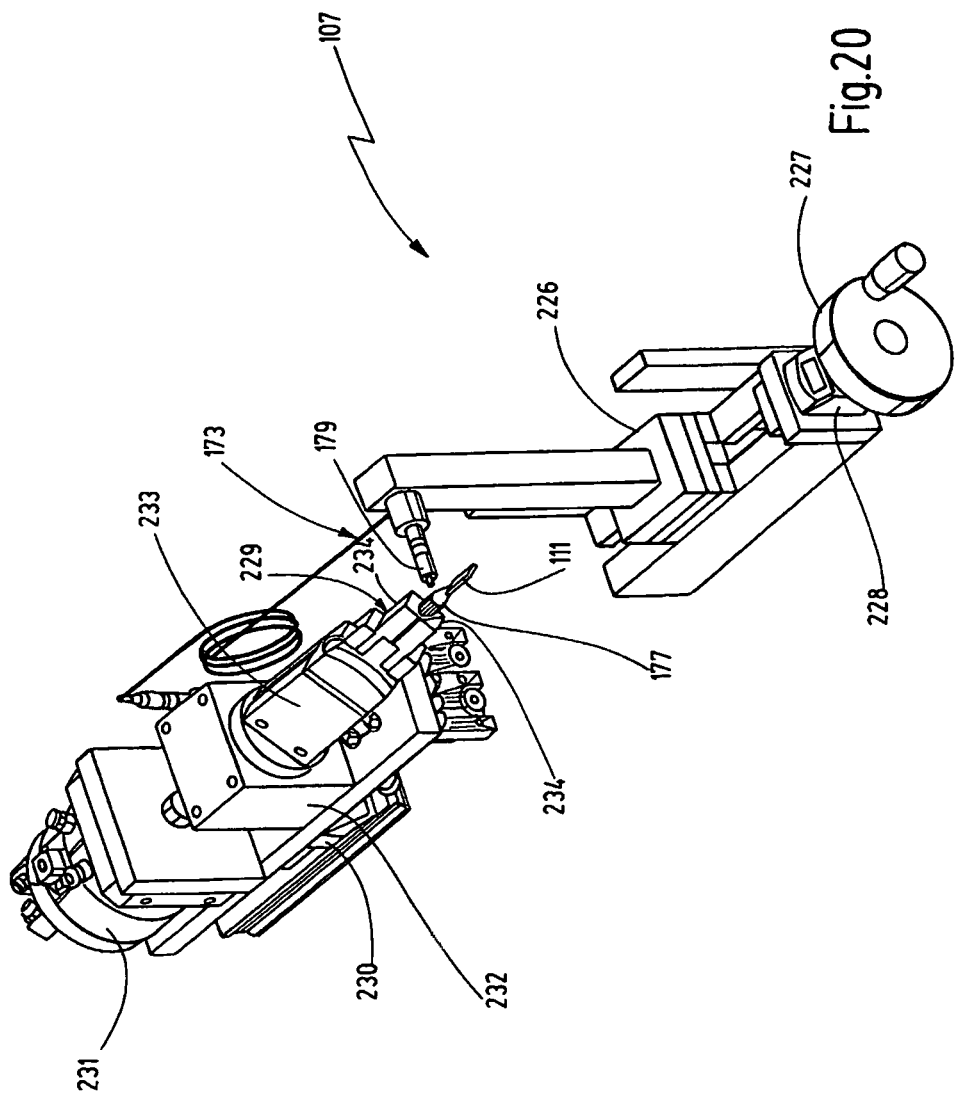

METHOD FOR ESTABLISHING THE PRESENCE OF SPECIFIED CHARACTERISTICS OF A CONTAINER PRODUCT AND DEVICE FOR PERFORMING SAID METHOD

FIELD OF THE INVENTION

The invention relates to a method for establishing the presence of specified characteristics of a container product. The container product is made of a plastic material in particular. Furthermore, the invention relates to a device for performing this method.

BACKGROUND OF THE INVENTION

Container products made of plastic materials are used in a wide variety of shapes, sizes and equipment as mass-produced products in wide distribution and for a wide variety of intended applications. In manufacturing, which for economic reasons must be conducted in a particularly economical manner in view of the large number of parts, quality control being conducted in close association with the respective manufacturing process is essential to recognize deviations of specified properties of the product from the respective target value and thereby to allow corrective procedures to be performed in the manufacturing plant before large quantities of rejects have been produced.

State of the art systems in this regard divert sample batches from the respective production line at predetermined intervals of time and test them for deviations in specified important use properties from the target value. This system has proven to be tedious and time-consuming, in particular when, to arrive at reliable test results, sample batches having a large number of containers must be tested, each being handled manually and inspected by trained inspection personnel for the presence of specified properties. The required time involved and the resulting personnel costs have a negative effect on the cost-effectiveness of production of these container products.

SUMMARY OF THE INVENTION

An object of the invention is to provide an improved method that creates a prerequisite for an improved profitability in the manufacture of container products through an efficient design of the quality control.

According to the invention, this object is basically achieved by a method where the actual value of at least one predetermined property is determined automatically in an inspection station of a testing device and is compared with the target value of this property. This procedure eliminates the need for having the corresponding test processes performed by inspection personnel, which leads to corresponding savings in time and personnel costs. In particular, with the container products to be manufactured in the large numbers in question here, this automatic inspection results in a significant improvement in profitability. In addition, the automation of inspection steps also achieves the result that subjective test areas, such as those that cannot be ruled out completely through the use of inspection personnel, have a negative effect on the measurement result. Since the test results can be compiled with a very high reliability, they can be forwarded directly to the manufacturing machine upstream in the process sequence to optimize its manufacturing process.

With a corresponding number of inspection stations to be used for testing, it is thus various essential product properties, such as weights, basically as a measure of the filling quantity of container contents, the wall thickness of the container, the applied force necessary for handling and/or use of a container and the like, can be efficiently established.

Container products with plastic containers can advantageously be manufactured in large numbers according to the known Bottelpack® method in such a way that the container product is created in the form of a container strip, with containers made of plastic, for example, as vials or ampoules, which are connected to one another so they can be separated at the connection points. In an advantageous exemplary embodiment of the method according to the invention, in a first inspection station of the testing device, the containers can be separated by machine, and the separation force required to separate the containers can be determined. Knowledge of the magnitude of the separation force makes controlling the manufacturing process possible in such a way that the connection point forms a sufficiently secure connection for strip sections being supplied for packaging and shipping. Also, the end user is capable of easily separating the respective containers to be used from the strip.

In the case of especially advantageous exemplary embodiments of the invention, containers are separated from the container strip by twisting in the first inspection station for this purpose. The torque required for twist-off is detected automatically.

With particular advantage, in the case of containers filled with container contents, the separated containers are moved by machine into a second inspection station, where they are weighed for an automatic determination of their total weight. After weighing, the weighed containers are moved by machine into a third inspection station, where they are emptied.

To determine the weight of the container contents, the emptied containers may be taken by machine to another inspection station and weighed there again to determine their tare weight. The total weight detected is automatically compared with the tare weight detected to determine the weight of the container contents.

In the case of containers having an end part associated with a removal area on a neck part, with the end part being removable from the main part of the container by a twisting movement, the containers may be moved by machine to an inspection station, where the end part is twisted off by machine and the torque required for twist-off is detected automatically. In the case of containers of the ampoule type, the end part on the neck is often a twist toggle, which can be removed from the neck part at an intended breaking point. Detecting the torque here provides information about whether the intended breaking point is designed suitably, so that the user can conveniently remove the end part. Similarly, with different types of containers such as vials, which have a removal area with screw closures on the neck part, a corresponding torque determination may signal the existence of use properties.

The containers may advantageously be moved by machine to an inspection station, where an incision, which exposes the cross section of at least a part of the container wall, is formed by machine. This procedure opens up the possibility of detecting the thickness of at least one cut container wall automatically after the cut containers have been moved by machine to another inspection station.

Instead of performing destructive testing of the container to detect the wall thickness in at least one measurement point on the container, this step may be omitted, and a nondestructive test of the container thickness may be performed in at least one location by testing the container with regard to its respective wall thickness, for example, by ultrasound or optical measurement methods. Nondestructive testing also has the advantage that none of the separation dust or sawdust that is formed in destructive testing of a container is formed. In this case, despite suitable suction exhaust, the possibility that dust or sawdust will have a negative effect on the measurement precision of other inspection stations cannot be completely ruled out.

In a final method step, for example, after detection of the wall thickness, the containers are preferably brought by machine to an ejection station and removed there from the test apparatus. The overall sequence of the method can then take place by machine without any procedures having to be performed by personnel. The individual process steps, taking into account the reference to the respective device inspection stations, may also be separated without interfering with the automatic character of the test processes. The test process steps may also be disposed in deviating constellations one after the other next to the devices.

The method according to the invention can also be expanded by additional test procedures. For example, any inscriptions on the top side of the container or in other regions can be detected by mechanical or optical scanning methods and then inspected with regard to the quality of the implementation and the thoroughness of the character information.

In addition to the methods described here, additional test methods may also be used in which, for example, by an ultrasound measurement or a laser measurement in different regions of the container and its parts. Their wall thickness can also be determined by using measurement methods in that regard, to ascertain the quantity of container content, while optionally incorporating acoustic measurement stations.

Based on the modular type of system pertaining to the individual test equipment with which the test methods described above can be performed, and which can also be easily adapted to different shapes of ampoules and container products, the possibility exists of testing container or ampoule products that are joined together in a strip, as well as individual containers or individual ampoules, as described above.

In addition to the method according to the invention, the measured values for at least a portion of the containers can preferably be detected by electronic detection, storage, and evaluation media, in at least one of the measuring inspection stations. Their measured values may be detected for at least some of the containers and stored for the purpose of obtaining a statistical analysis of the direction in which (trending), and the amount by which, the actual values of the inspection stations thereby determined can be removed from the target value specifications. The differential values obtained between the actual value specification and the target value specifications are relayed to a machine control unit of a manufacturing device, with the provision that the manufacturing parameters are to be optimized during or at the start or at the end of the manufacturing process such that the differential values approach zero, or the manufacturing material to be supplied to the manufacturing device is adjusted in its material properties.

Thus, if ascertained statistically that the container contents are in excess of or less than the target value specifications determined on the basis of the volume, then the manufacturing equipment can be instructed to feed a greater or lesser filling amount into the respective container on the basis of the statistical analysis. If the torque values in shearing off or twisting off in one direction or the other direction do not prove to be adequate based on the target value specifications, by changing the plastic material used or by changing the wall thickness, the required values can also be achieved during the manufacturing process. If minor differential values between the actual value specified and the target value specified can be detected and the aforementioned statistical analysis reveals trends in the development of the manufacturing, deviations can then be effectively counteracted. In an expansion of the measures described above, the statistical analyses can also be filed and documented accordingly, so that the history of the manufacturing method can be disclosed at the time of customer acceptance of the manufacturing equipment and/or the container products.

The subject matter of the invention is also a device for performing the method. Advantageous embodiments of the device are disclosed.

Advantageously, in particular to have a configuration of a container product in the form of a container strip, with containers made of plastic joined separably to one another at connecting points, a first inspection station has a separation device for mechanical separation of the containers by mechanical twist-off from the container strip.

In a particularly preferred exemplary embodiment, the first inspection station for the respective container to be separated from the container strip may have a holder, which encompasses this container strip at least partially. This holder is rotatable by a rotary drive for twisting off the container. The rotary drive has a torque sensor for detecting the twist-off torque.

In a particularly advantageous manner, the device may be designed such that a transport mechanism is provided, having receptacles that can be assembled with a respective container through the first inspection station. The receptacles can be moved to additional inspection stations disposed along an inspection zone.

The transport device expediently has a motor-driven carousel that moves the receptacles along a circular test zone to additional inspection stations disposed along the test zone.

Alternatively, the inspection stations can be disposed along a test zone extending in the longitudinal direction. A transport device has a transport element that moves the containers from one inspection station to the next in succession.

Other objects, advantages and salient features of the present invention will become apparent from the following detailed description, which, taken in conjunction with the drawings, discloses preferred embodiments of the present invention.

BRIEF DESCRIPTION OF THE DRAWINGS

Referring to the drawings that form a part of this disclosure:

FIG. 19 is a perspective view, slightly enlarged in comparison with FIG. 2, illustrating a fifth inspection station with a device for twisting off a container end part according to the second exemplary embodiment of the invention; and FIG. 20 is a perspective view, shown on an enlarged scale, of a partial region of a seventh inspection station with a device for measuring container wall thicknesses according to the second exemplary embodiment of the invention.

DETAILED DESCRIPTION OF THE INVENTION

The method according to the invention and the device provided for carrying it out are explained below on the basis of two examples in which a container product in the form of a container strip made of plastic has a series of containers of an ampoule-type shape designed in one piece with the strip. Those container products can be produced, for example, according to the known Bottelpack® system in a combined blow molding, filling and sealing process. The method according to the invention can equally be performed with different types of containers.

Figure 1:
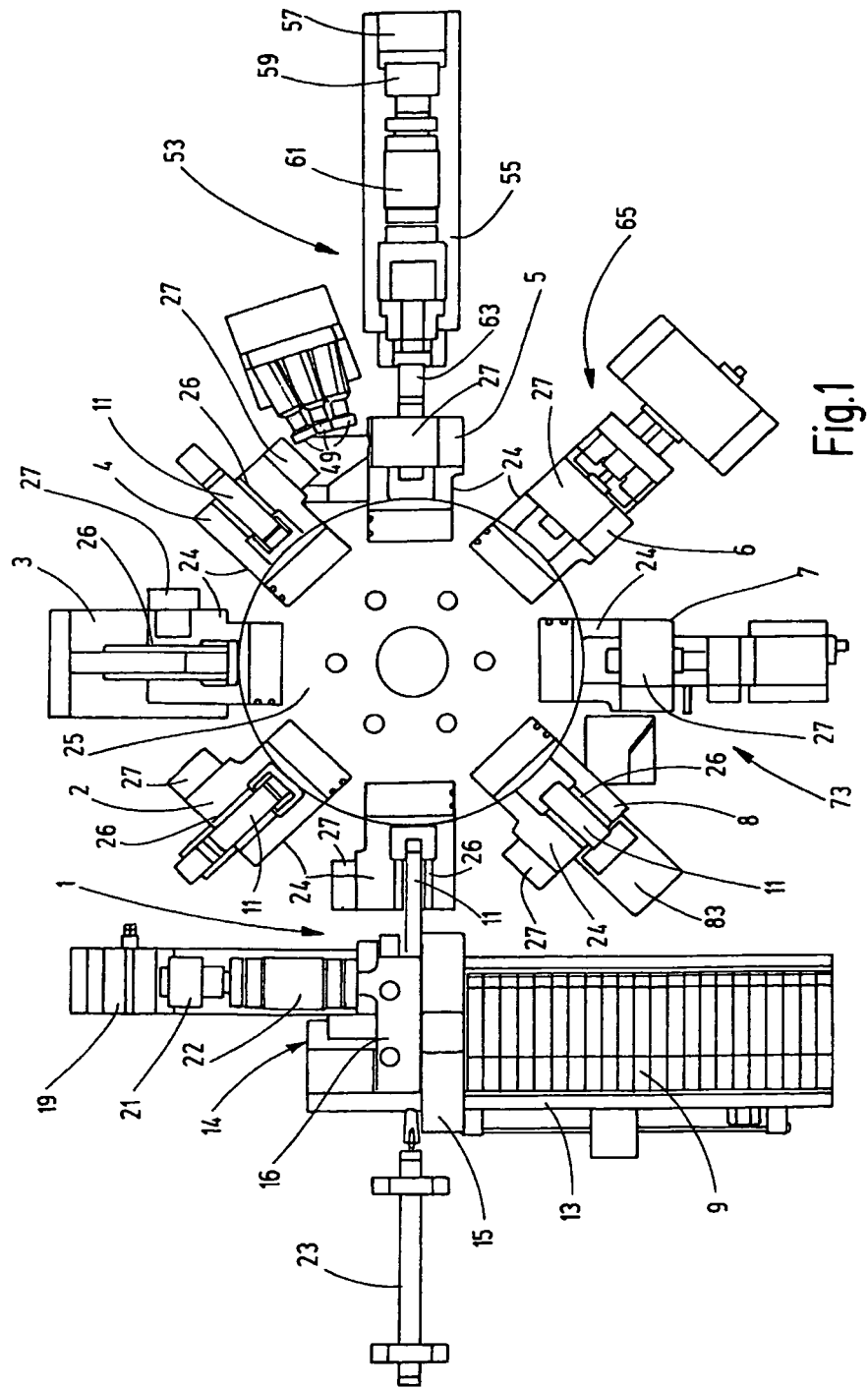
FIG. 1 is a highly schematic and simplified top plan view of a device according to a first exemplary embodiment of the invention for performing the method according to the invention.
Figure 2:
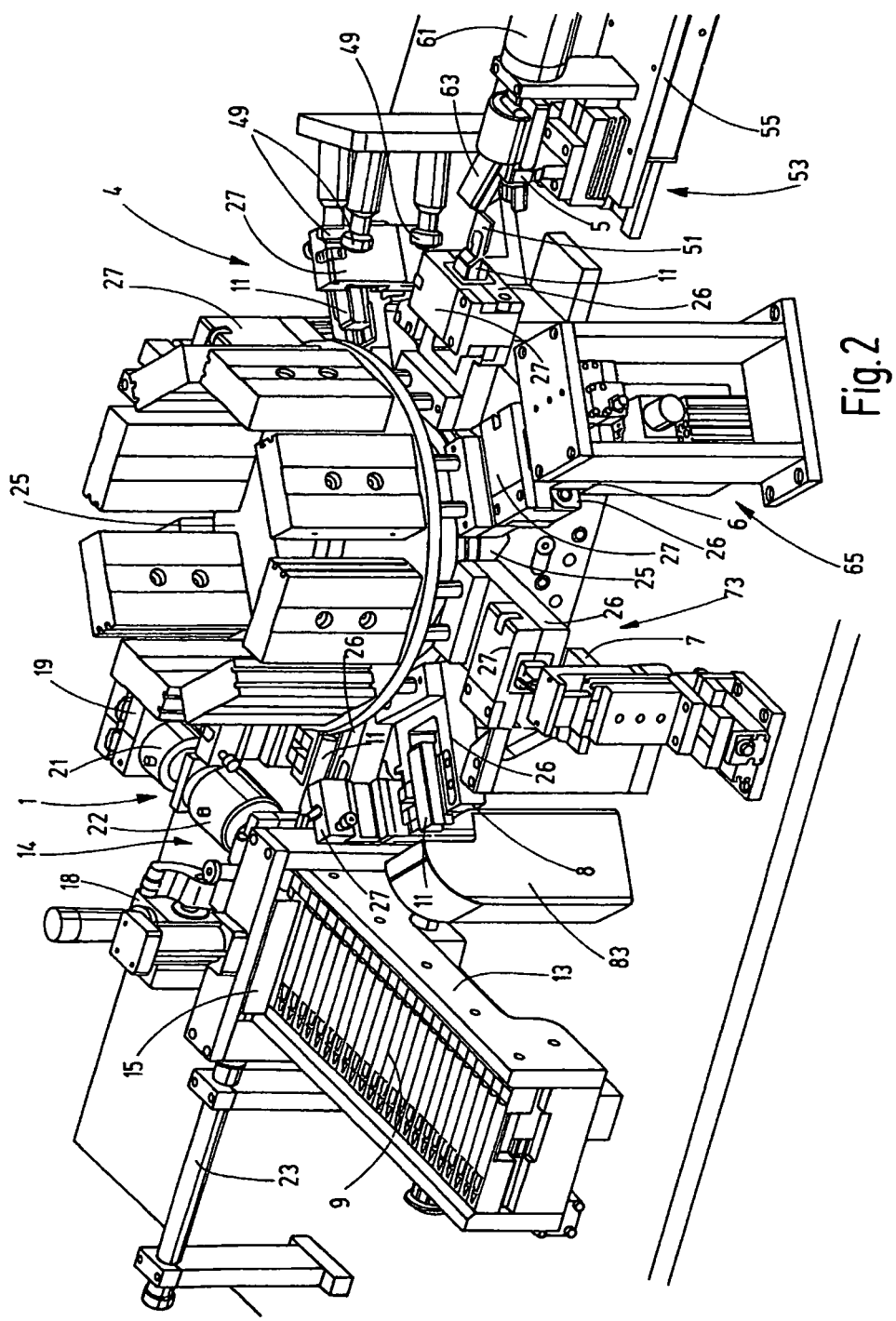
FIG. 2 is a schematic and simplified, perspective view of the device of FIG. 1.

The first exemplary embodiment of the device, shown in FIGS. 1 and 2 in an overall diagram and in FIGS. 3 through 10 in partial diagrams, has a plurality of stations into which a container 11, about whose properties a finding is to be made, is introduced by machine in succession. The stations are indicated in highly schematic and simplified diagrams in FIG. 1 and not all of them are visible in FIG. 2. These stations include (see FIG. 1) a first inspection station 1, a second inspection station 2, a third inspection station 3, a fourth inspection station 4, a fifth inspection station 5, a sixth inspection station 6, a seventh inspection station 7 and an ejection station 8. As already mentioned, in the present invention, a carrier or container strip 9 has a series of ampoule-type containers 11 that are connected to one another at connection points 12. The connection points 12 form an intended breaking point for the separation of the containers 11 from the container strip 9.

Figure 3:
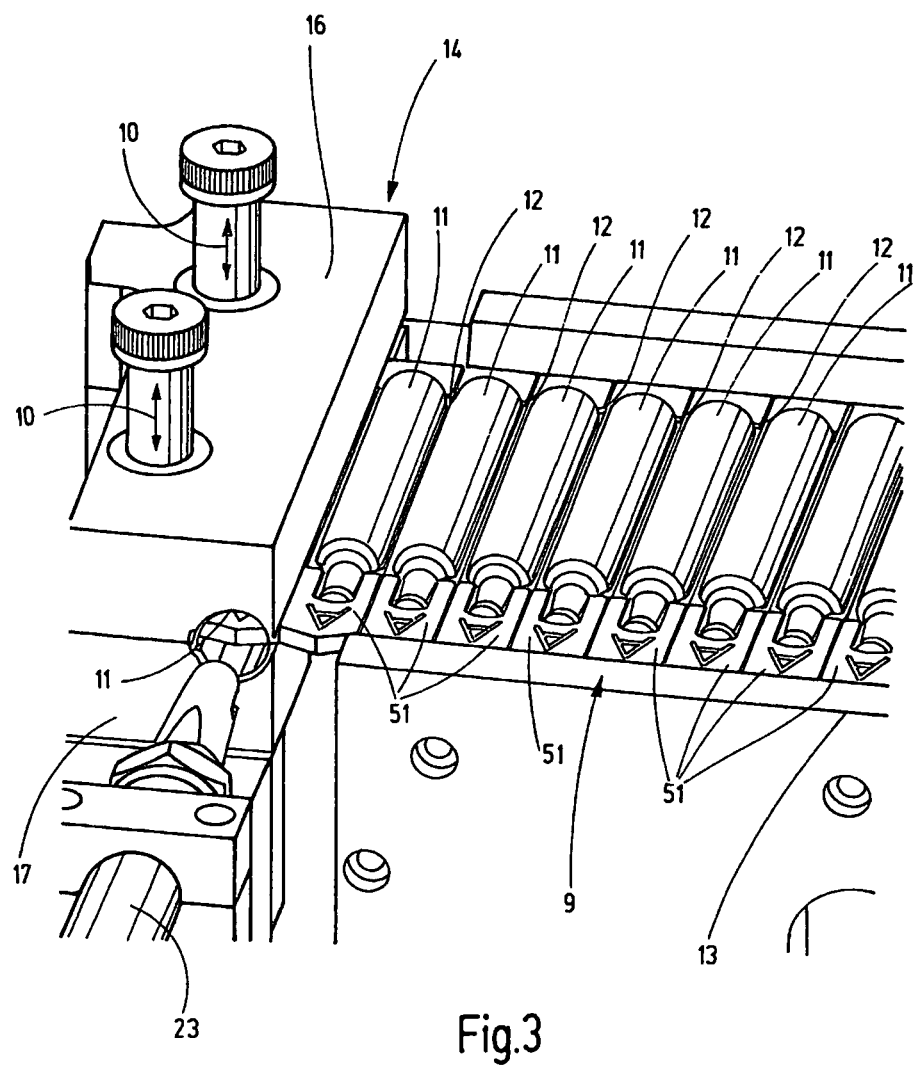
FIG. 3 is a perspective view on a larger scale of only a partial detail of a first inspection station of the device of FIG. 1 having a separating mechanism.
Figure 4:
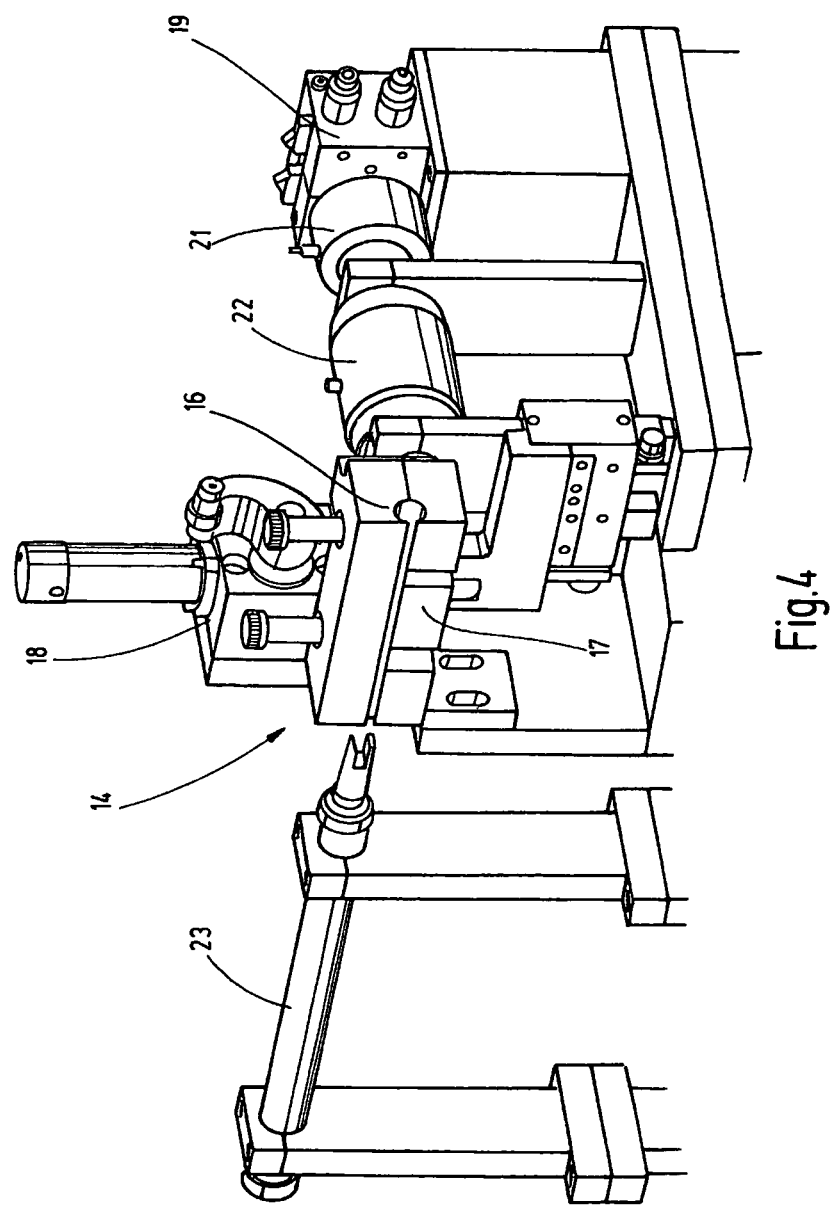
FIG. 4 is a perspective oblique view of the first inspection station of FIGS. 1 and 2 shown on a slightly smaller scale than FIG. 3.

As shown in FIGS. 1 to 3, the container strip 9 is moved by a conveyor 13 up to the first inspection station 1. The conveyor 13 is designed as a stepping conveyor that moves, with each advancing step, a container 11 into a separation position in which a separation device 14 separates the last container 11 in each case. The separation device 14 has a movable hold-down device 15 (see FIG. 2 in particular), which secures the next to last container 11 of the strip 9 for a respective separation operation. To separate the last container 11 in the separation position, the separation device 14 has a holder for the container 11 that is to be separated, as shown best in FIGS. 3 and 4, with movable jaws 16 and 17, which surround the container 11 to be separated in the closed position shown in FIGS. 3 and 4.

The upper haw 16 in the drawing, as indicated with arrows 10, can be moved by an actuator 18 for the movement between the closed position illustrated here and an open feed position, in which the container 11 to be separated is accommodated between the jaws 16 and 17. Both jaws 16, 17 with the container 11 held between them, can be rotated by a rotary drive 19 for twisting off at the connection point 12. From this location, the driving torque is transferred to the jaws 16, 17 via a safety coupling 21 and a torque sensor 22. For determining whether the properties of the connecting point 12 correspond to the target state, the twist-off torque determined by the rotary torque sensor 22 is detected. After completing the separation, with the jaws 16, 17 moved back into the starting rotational position, the container 11 is pushed out of the jaws 16, 17 by a machine-operated slide 23 and reaches a position in which it is in a receptacle 24 of a transport carousel 25, as shown most clearly in FIG. 1 (see FIG. 1).

Figure 5:
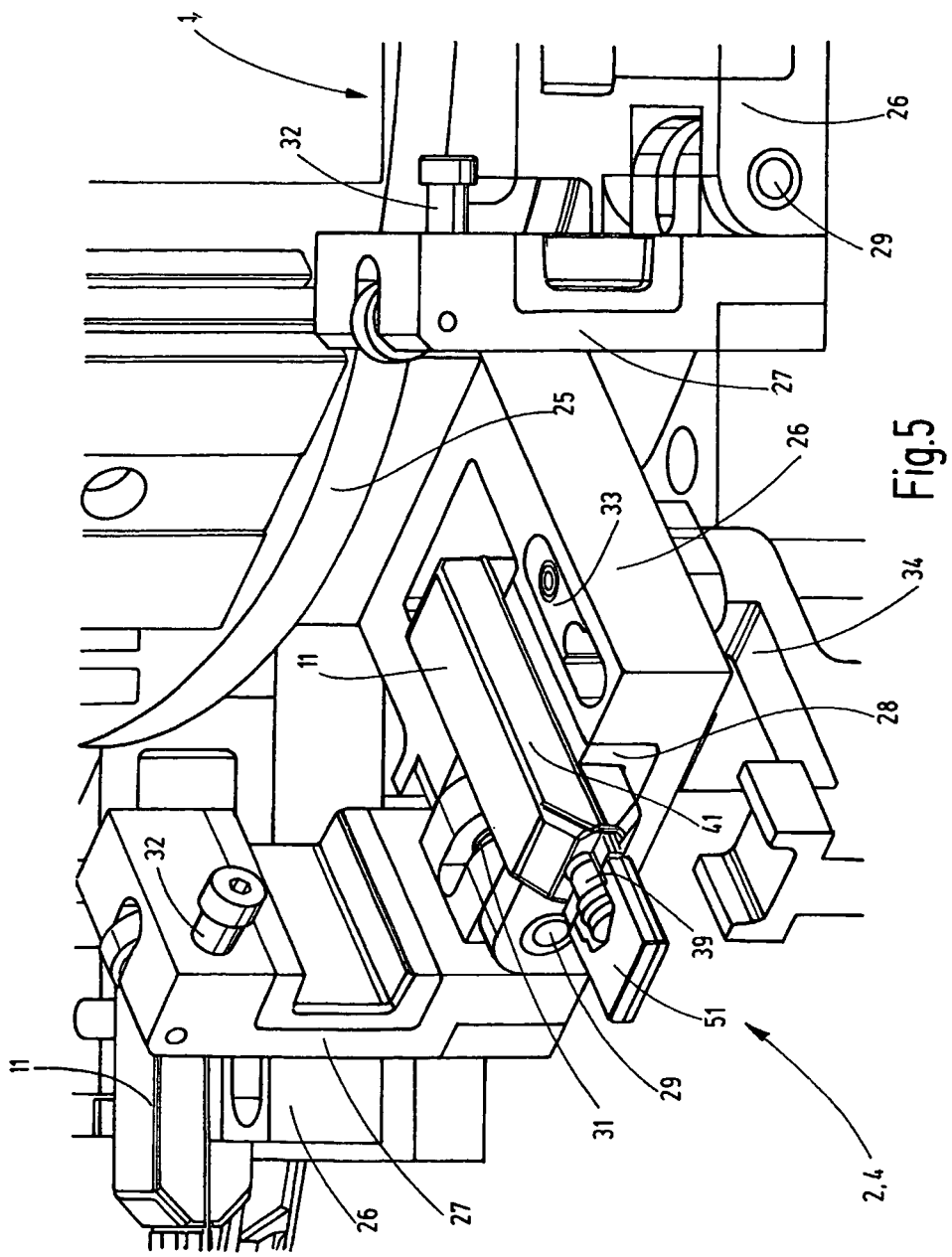
FIG. 5 is an enlarged perspective view of a part of FIG. 2 in mainly the region of a second inspection station having a weighing stand.

The motor-driven carousel 25 has eight of these receptacles 24 distributed uniformly on its circumference, and moves them along a circular test zone on which inspection stations 1 through 7, as well as ejection station 8, are disposed. The receptacles 24 each have a bearing part 26 for the respective container 11 as well as a movable cover part 27, the details of which can be seen most clearly in FIG. 5. As shown in FIG. 5, the bearing part 26 has a seat 28 for the respective container 11. The cover part 27 is hinge-mounted on the bearing part 26 by a hinge 29 on whose articulated axis a rotary spring 31 is disposed, prestressing a cover part 27 into the open position illustrated in FIG. 5. The cover part 27 has a bar journal 32 which, when the cover part 27 is pivoted into the closed position against the force of the rotary spring 31, engages with a bar slide 33, which is spring prestressed in the locked position. In the case of displacement of the bar slide 33 out of the bar position, the cover part 27 automatically moves back out of the closed position and into the open position illustrated in FIG. 5. As shown in FIGS. 1 and 2, the cover parts 27 in the inspection stations 1 through 4 and at the ejection station 8 are each shown in the open position. In test positions 5 through 7, each cover part 27 is in the closed position. In the closed position, the respective container 11 is secured with its container main part 41 in the seat 28 of the bearing part 26.

Figure 6:
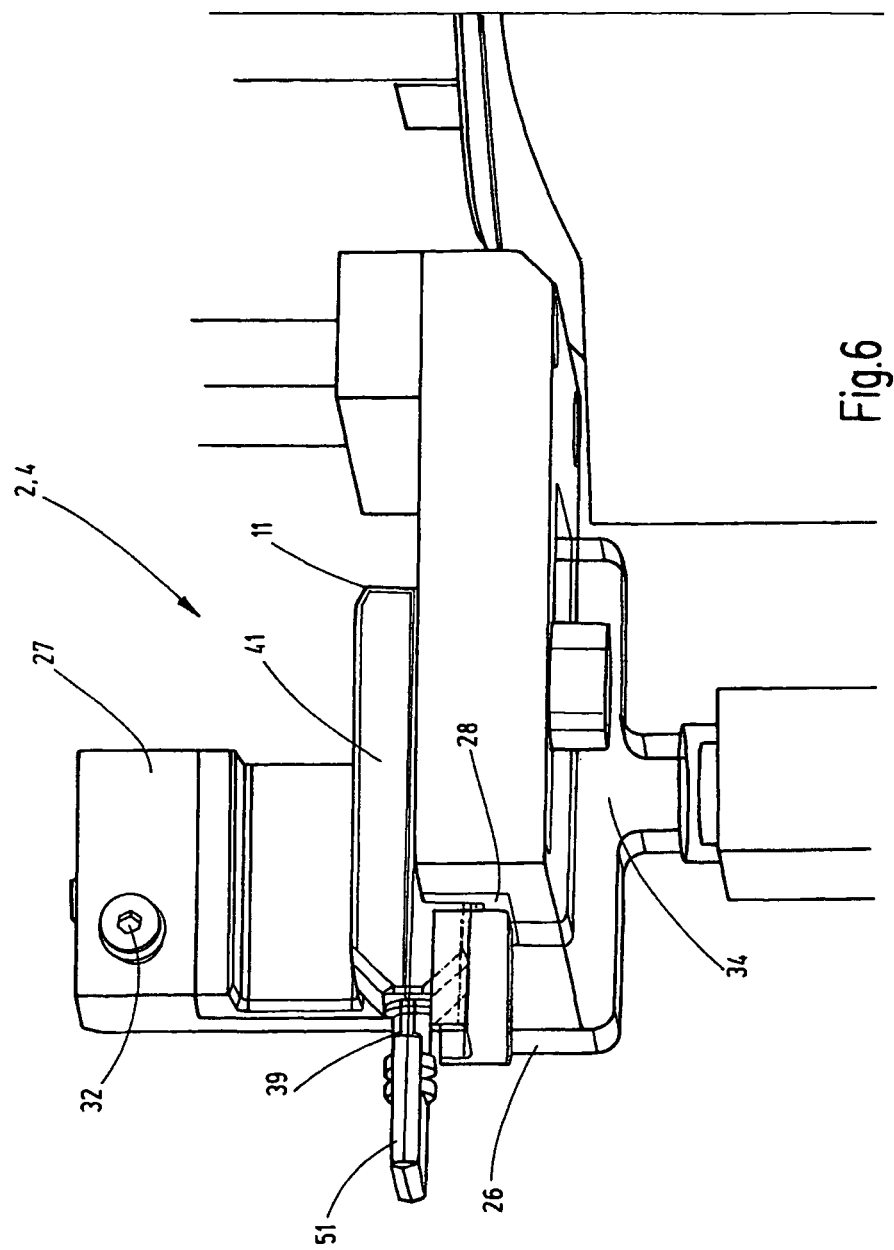
FIG. 6 is an enlarged perspective oblique view of part of the weighing stand of the second inspection station of FIG. 5.

Since the twist-off torque in separating the container 11 from the container wall 9 was detectable in the first inspection station 1, and the separated container 11 is moved into the respective receptacle 24 on the carousel part 25, this container 11 goes into the inspection station 2 through a rotational step of the carousel 25. Inspection station 2 is a weighing station for automatic detection of the total weight of the filled container 11. FIGS. 5 and 6 show details of the weighing stand. A vertically movable weighing element 34 functions as a type of weighing dish and can be displaced upward, out of the lowered position shown in FIG. 5, to raise the container 11 up from the seat 28 of the bearing part 26 by acting on its forward end and on its rear end in to determine the weight of the raised container 11. As shown in FIGS. 5 and 6, the cover part 27 is in the open position here.

Figure 7:
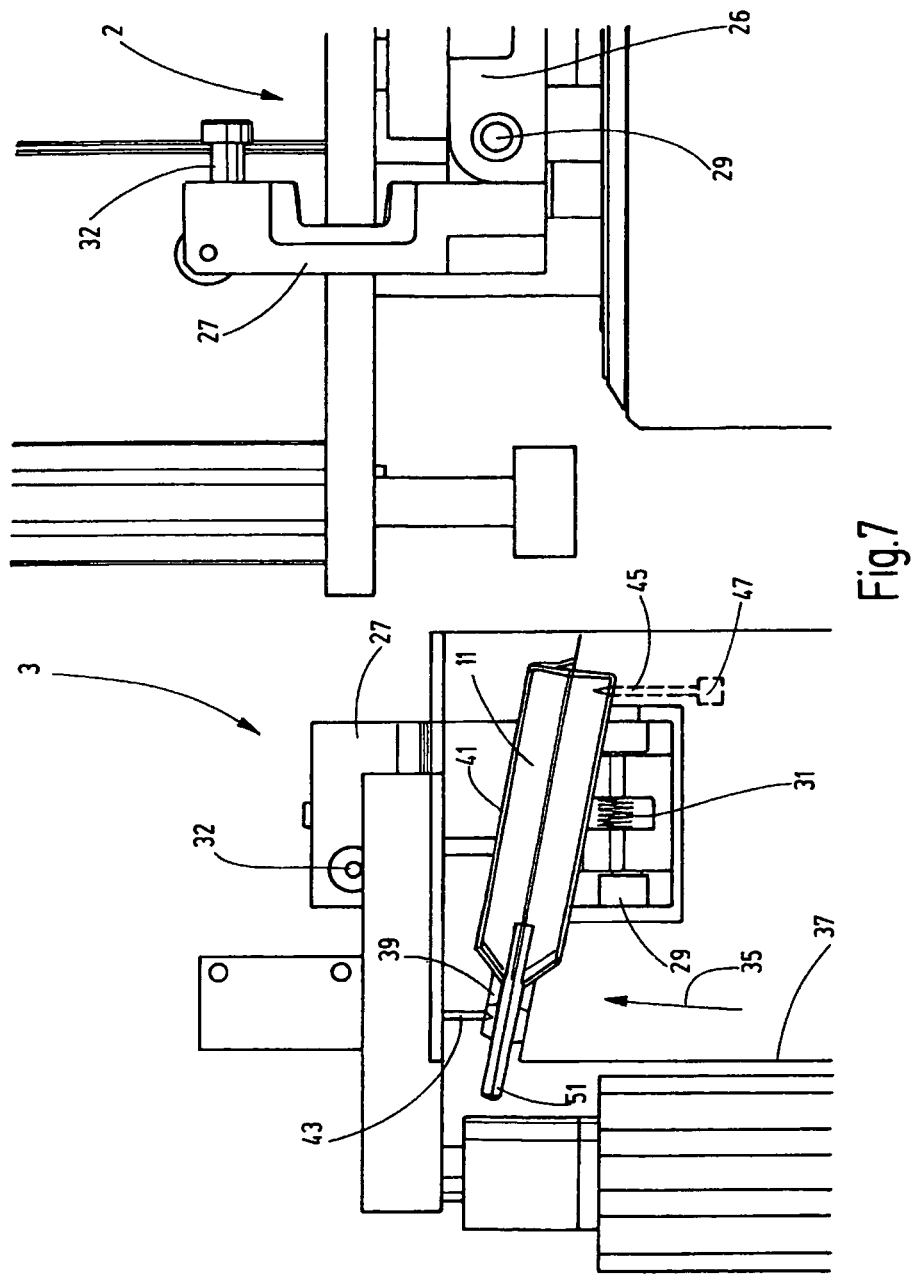
FIG. 7 is a side view of a third inspection station of FIGS. 1 and 2 having an emptying device, this view being enlarged in comparison with FIGS. 1 and 2, while at the same time being simplified in a highly schematic manner.

After detecting the total weight, the weighed container 11 goes to the inspection station 3 that has a device for emptying the container contents. The important details of the emptying device can be obtained from FIG. 7. As FIG. 7 shows, the inspection station 3 has a support 37 for the container 11, which support is movable in the direction of an arrow 35 and brings the container into an oblique or angled position in which the neck part 39 of the container 11 is at a higher level than the bottom end of the container main part 41. For emptying the container contents, a vent hole is formed by a movable puncturing needle 43 on the neck part 39, while a movable cannula 45 forms an emptying opening on the bottom part of the main part 41 of the container 11. The cannula 45 has a suction connection 47 for evacuating the container 11.

In the next transport step of the carousel 25, the emptied container 11 moves out of the inspection station 3 to the inspection station 4, which is a second weighing station corresponding in structure and function to the inspection station 2, already described with reference to FIGS. 5 and 6. Now the tare weight of the container 11, which was emptied previously, is detected. Thus, the mass of the container contents is established as the test result by the total weight/tare weight comparison.

Figure 8:
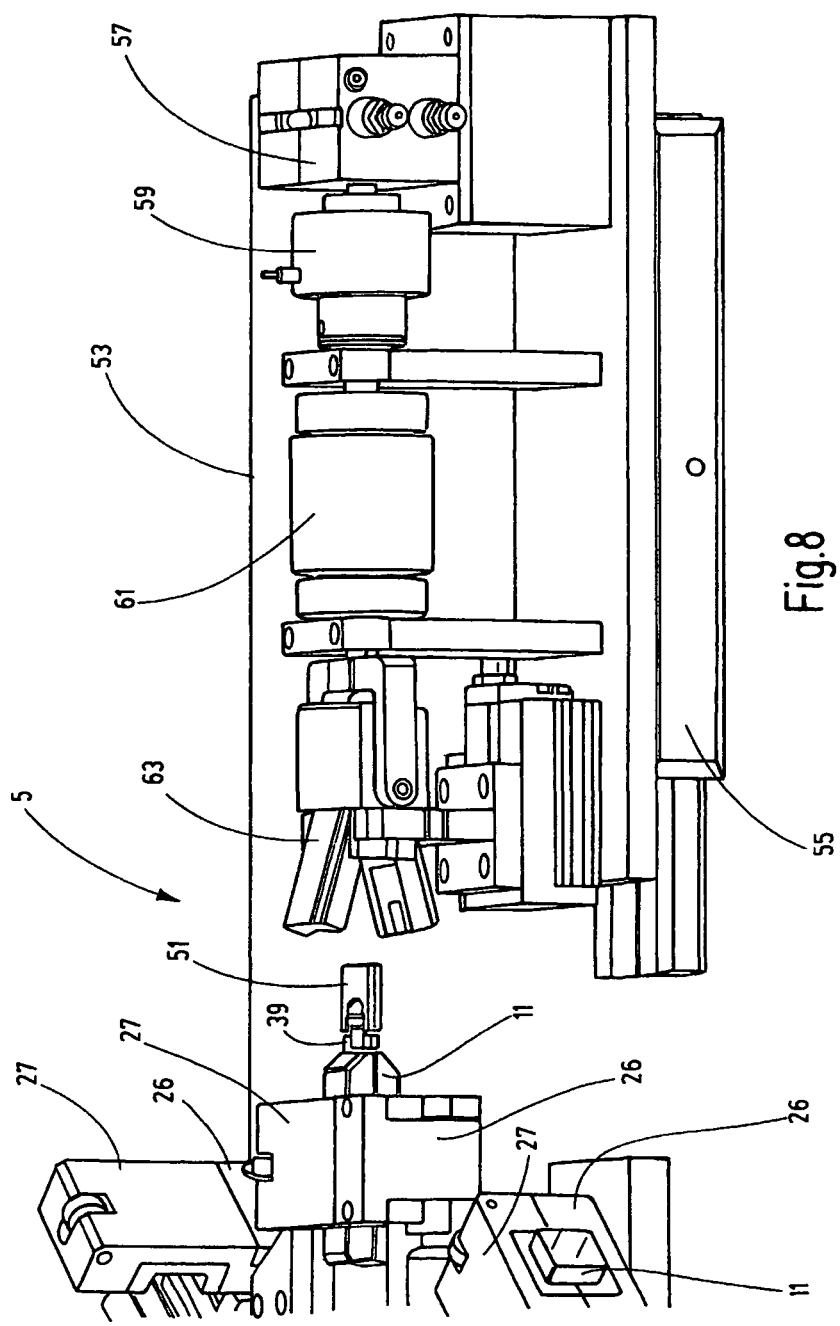
FIG. 8 is a perspective view of a fifth inspection station of FIGS. 1 and 2 with a device for twisting off a container end part, this view being shown on a slightly larger scale in comparison with that of FIG. 2.
Figure 9:
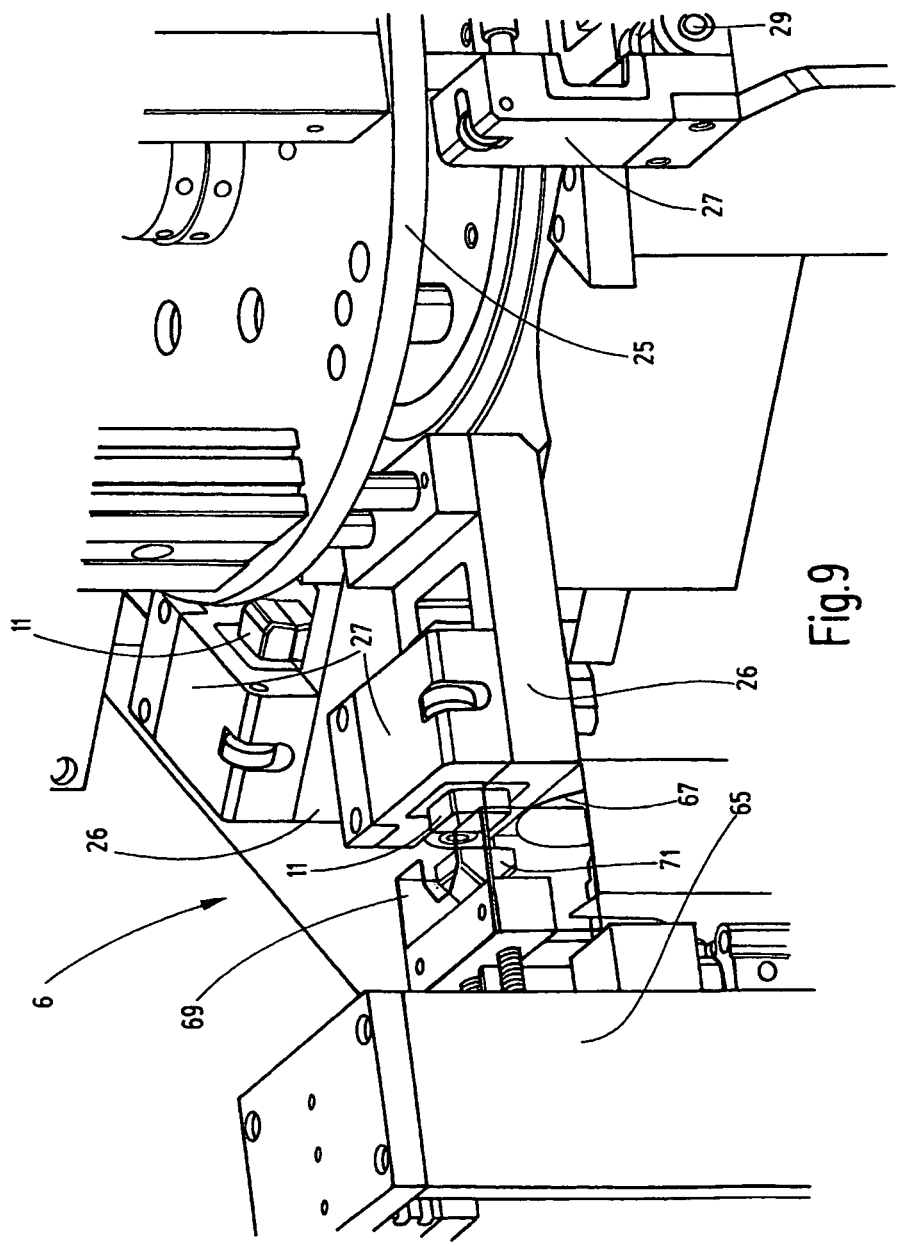
FIG. 9 is a perspective view on a slightly enlarged scale in comparison with FIG. 2 and illustrates mainly the region of a sixth inspection station of FIGS. 1 and 2 having a cutting device.

In the wake of the transport step to the following inspection station 5, the cover part 27, which is in the open position, as shown in FIGS. 1 and 2, comes into contact with a control unit having control rollers 49. Control rollers 49 pivot the cover part 27 engaged thereon into the closed position where the twist lock 32 engages with the slide bar 33 so that the cover part 27 is secured in the closed position. In this position the container 11 is secured in the seat 28 of the bearing part 26. FIG. 8 shows further details of the respective inspection station 5, which has a twist-off device 53 that removes an end part in the form of a twist toggle 51 integrally molded on the neck part 39 of the container 11. By twisting twist toggle 51 off of the container 11, twist-off device 53 determines the torque required for this twist off. The twist-off device 53 has a twist-off unit, displaceable on a carriage 55 and drives a controllable locking pliers 63 with a rotary drive 57 by a safety coupling 59 and a torque sensor 61. The locking pliers 63 grip the twist toggle 51 so that the twist-off toggle can be twisted off by the drive 57. The twist-off torque thereby detected signals whether the connection of the twist toggle 51 to the container 11 corresponds to the target condition.

The next inspection station 6 (FIG. 9) along the test zone has a cutting device 65 with a circular saw 67 that forms a cut, in the form of a cross section through the container 11. Saw 67 severs the front part 71 from the remaining main part 41 of the container 11, within a cutting zone with a safety shell 69 made of plexiglass.

Figure 10:
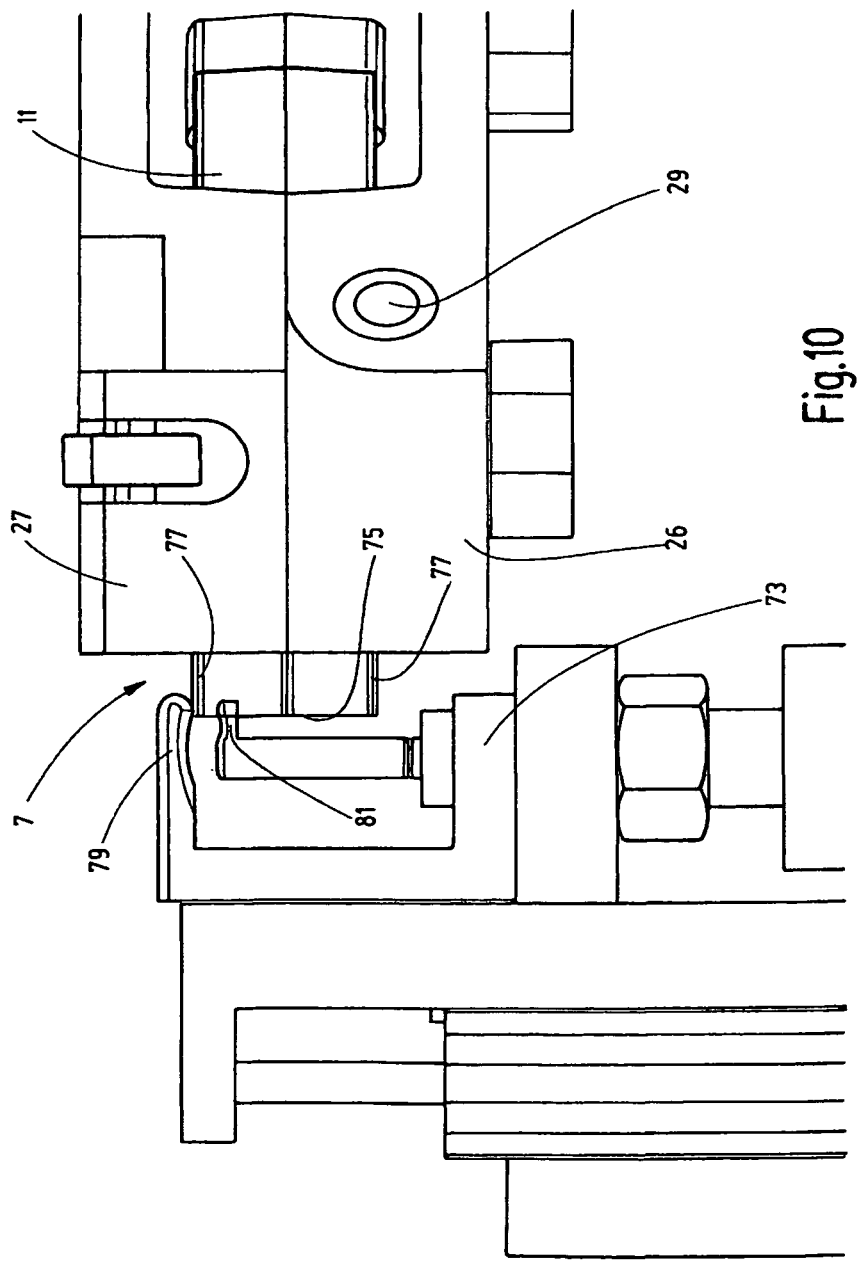
FIG. 10 is a side view of a partial region of a seventh inspection station of FIGS. 1 and 2, shown on an enlarged scale and having a device for measuring container wall thicknesses.

In the next step, the cut container 11 goes to the inspection station 7 (FIG. 10) that has a measuring device 73 for detecting the wall thickness of the container walls 77 exposed at the cut location 75. The measuring device 73 has movable measuring calipers 79 and 81 for this purpose. These calipers are movable for examining the upper wall 77 and the lower wall 77 in FIG. 10. FIG. 10 shows the measuring operation of the upper wall 77 before the caliper 81 has come in contact with the inside of this wall 77.

After detecting the actual wall thickness value in inspection station 7, the container 11 then goes to the ejection station 8, which ejects the inspected container 11 into a waste collector 83.

The second exemplary embodiment of the device according to the invention, as shown in FIGS. 11 through 20, differs from the first exemplary embodiment fundamentally in that, instead of a test zone with inspection stations 1 through 7 disposed on a circular path, supplied with the containers 11 to be inspected by means of a transport device in the form of a carousel conveyor, an inspection zone extending in a longitudinal direction 220 is provided.

Figure 11:
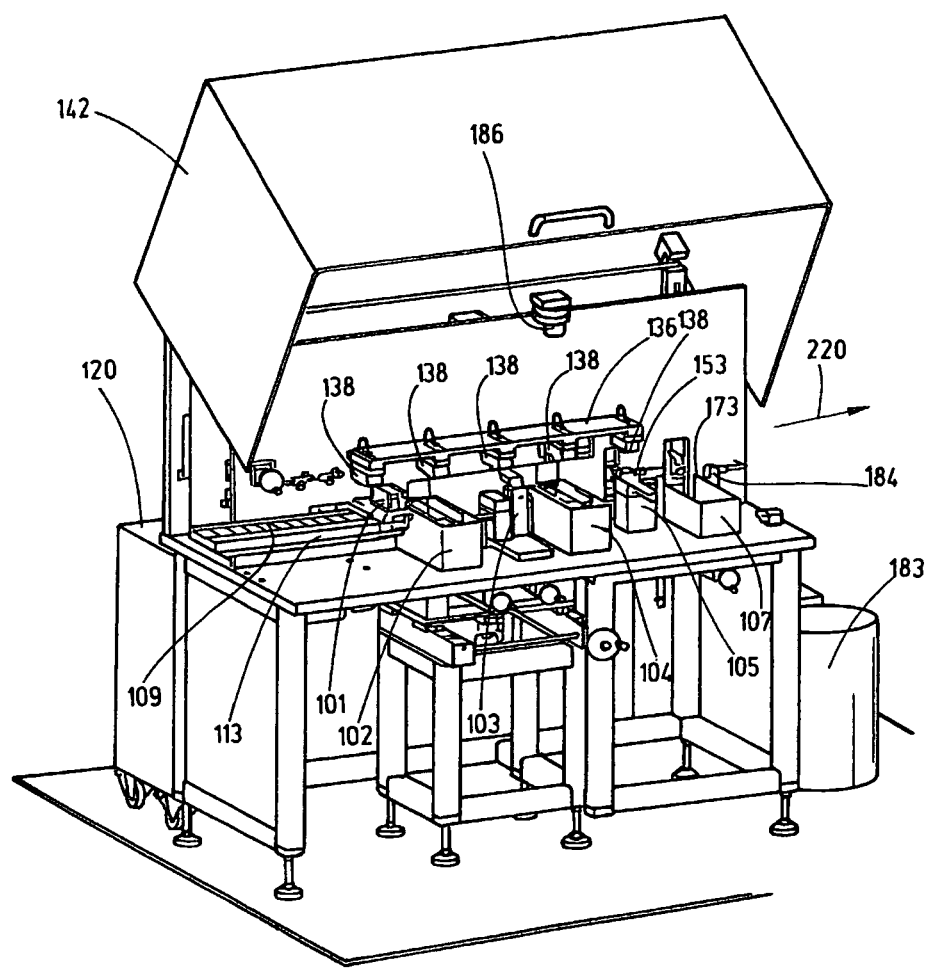
FIG. 11 is a highly simplified and schematic perspective view of a device according to a second exemplary embodiment of the invention.
Figure 12:
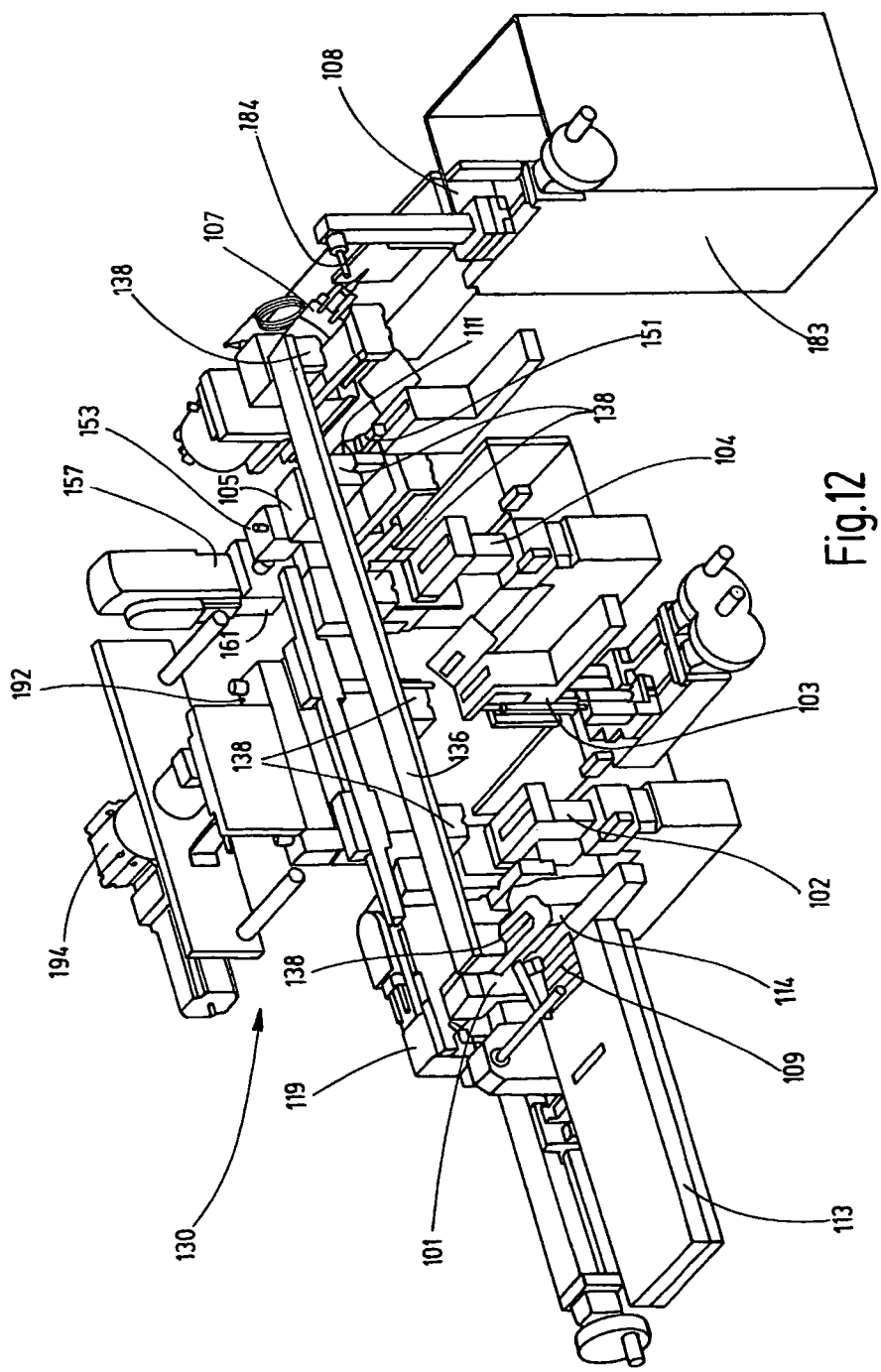
FIG. 12 is a perspective view, which is also highly simplified and schematic and is drawn on a larger scale than FIG. 11 of the exemplary embodiment according to FIG. 11, with the successive inspection stations and the associated transport device being successive in the longitudinal direction.
Figure 13:
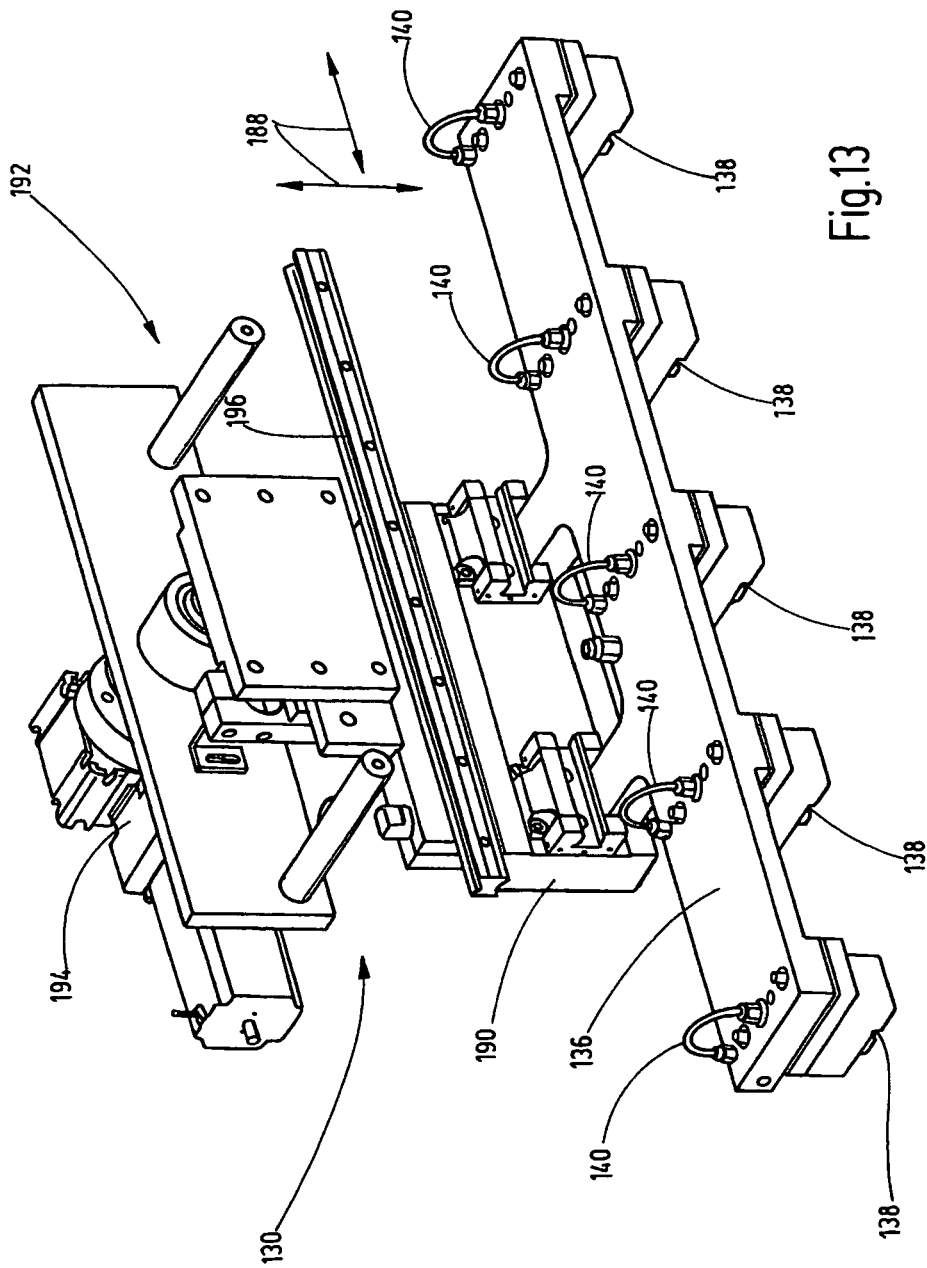
FIG. 13 is another perspective view, drawn an enlarged scale, showing only the transport device of the second exemplary embodiment of the device.

In the second exemplary embodiment of the device shown in FIGS. 11 and 12 in overall diagrams and in FIGS. 13 to 20 in partial diagrams, a plurality of stations into which a container 111, about whose properties a finding is to be made, are placed successively by machine. These stations are illustrated in simplified form in FIGS. 11 and 12, but not all the stations are visible in FIG. 12.

As FIG. 11 shows, the inspection zone is disposed on a frame 120 with a covering hood 142. A camera 186, situated above the inspection zone, permits monitoring of the operation from the outside, even with the cover hood 142 closed.

The individual stations include (see FIGS. 11 and 12) a first inspection station 101, a second inspection station 102, a third inspection station 103, a fourth inspection station 104, a fifth inspection station 105, a seventh station 107 and an ejection station 108. The sixth inspection station, which is required in the first exemplary embodiment, has been eliminated in the second exemplary embodiment for reasons to be explained below.

Figure 14:
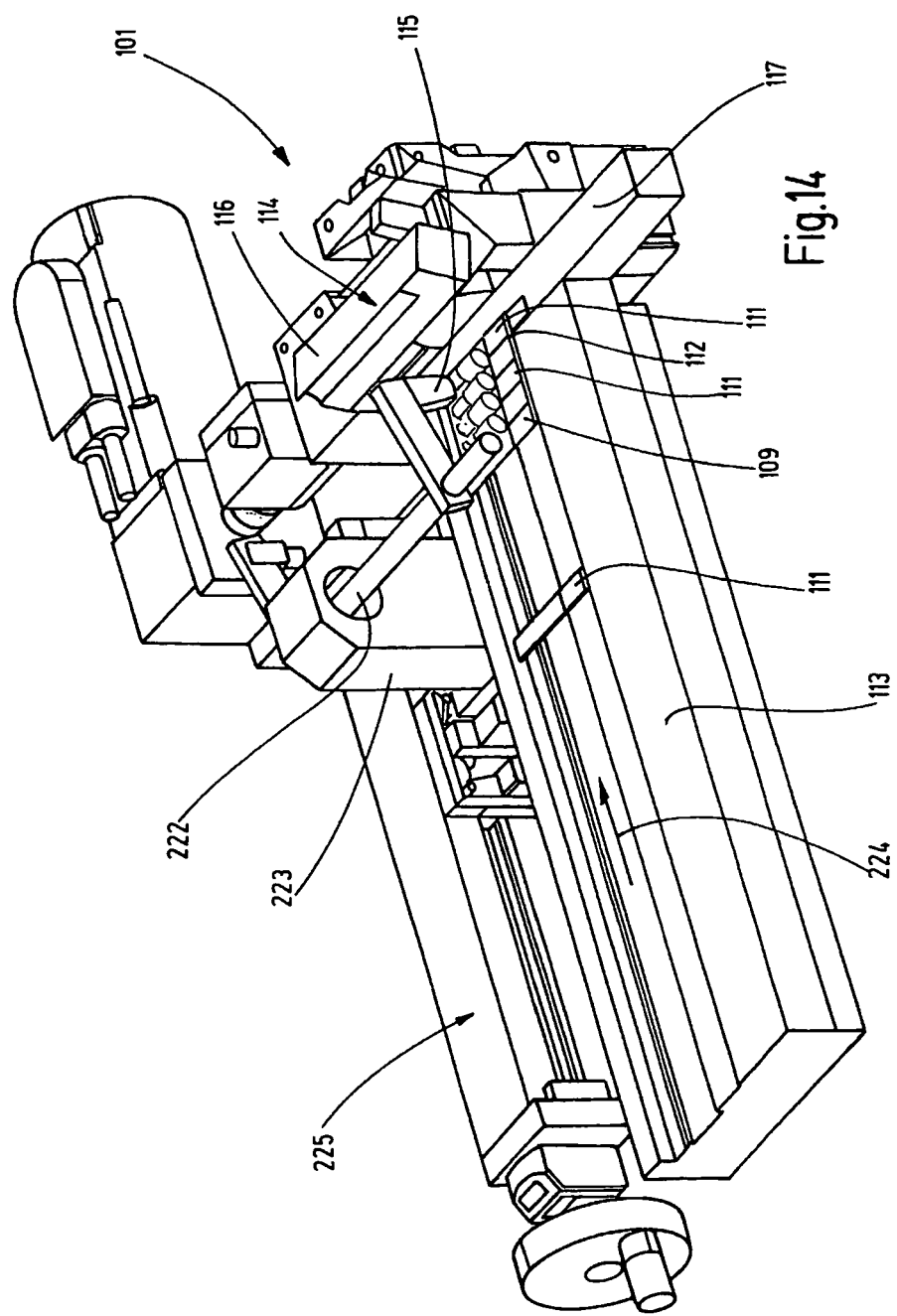
FIG. 14 is a perspective view, drawn on a larger scale, showing only a partial detail of a first inspection station having a separation device according to the second exemplary embodiment of the invention.

As already mentioned, in the present example a carrier strip 109 has a series of ampoule-shaped containers 111. The containers are interconnected at connecting points 112, which form a type of intended breaking point for the separation of the containers 111 from the container strip 109. Containers 111 have a bulging shape as shown at the right in the direction of viewing in FIG. 14, with a single container 111 formed as a flat product to the left of this at a distance. As shown in FIGS. 11, 12 and 14, the container strip 109 is supplied by machine to the first inspection station 101 by a conveyor 113. The conveyor 113 is designed as a stepping conveyor that moves one container 111 at a time into a separation position with each forward step. In this position a separation device 114 separates the last container 111 in the row. The separation device 114 has a movable hold-down device 115 (see FIG. 14 in particular) that secures the next to last container 111 of the strip 109 for a respective separation operation. The hold-down device 115 is an L-shaped part that can be pivoted at its other end about a pivot axis 222. To achieve the forward advance, the pivot axis 222 is supported on a bearing block 223, which is movable in the forward direction 224 by an advancing mechanism 225.

Figure 15:
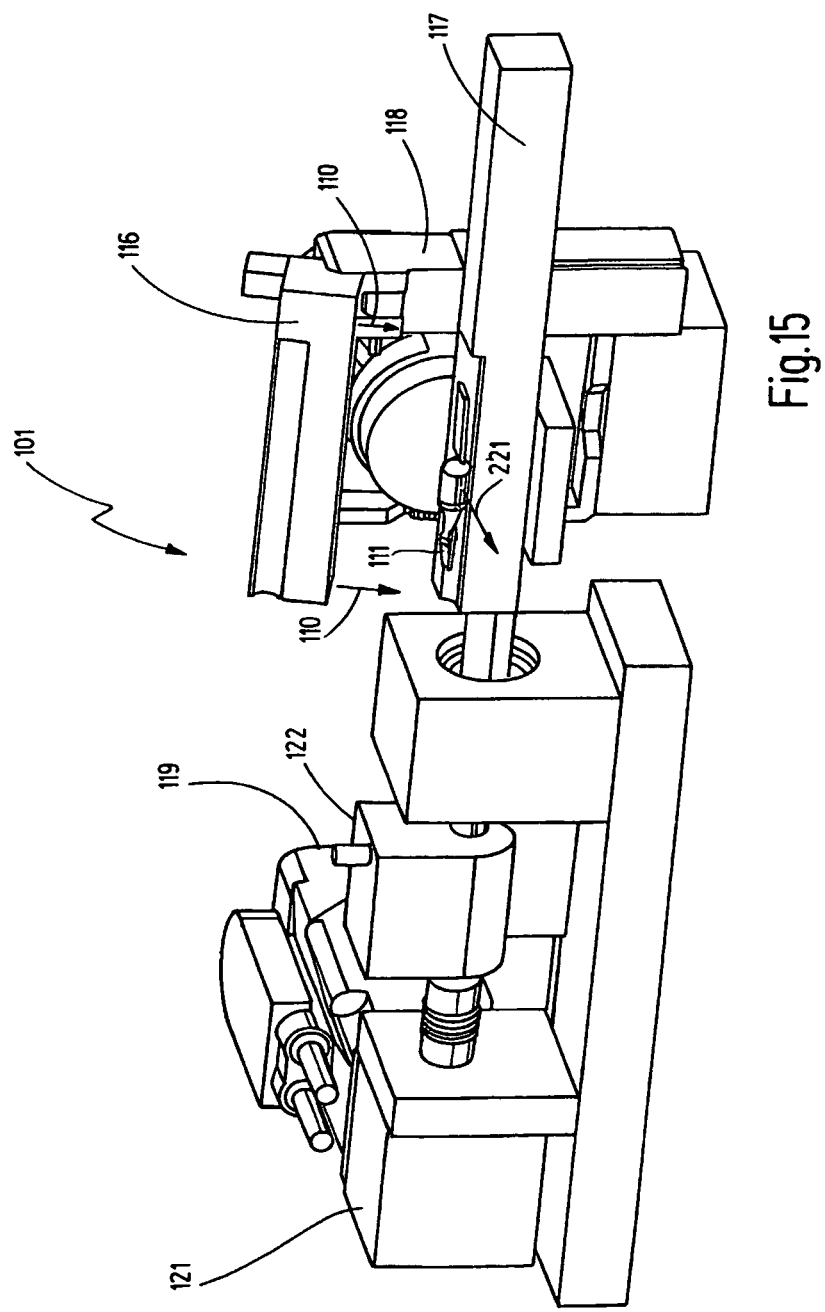
FIG. 15 is a perspective view of the first inspection station according to the second exemplary embodiment of the invention.

To separate the last container 111 in the separation position, the separation device 114 has a holder with movable jaws 116 and 117 for the container 111 to be separated, as shown best in FIGS. 14 and 15. In the open position shown in FIGS. 14 and 15, these jaws grip the container 111 to be separated. For the movement between the open position shown here and a closed position, in which the container 111 to be separated is clamped between the jaws 116 and 117, the upper jaw 116 in the drawing, as indicated with arrows 110, is movable by an actuator 118. The two jaws 116, 117, with the container 111 gripped between them, can be rotated about an axis of rotation 221, which extends parallel to the longitudinal direction 220, by a rotary drive 119 for twisting off the connection point 112. The rotary drive transfers the driving torque, via a safety coupling 121 and a torque sensor 122, to the jaws 116, 117. The twist-off torque determined by the torque sensor 122 is detected automatically for determining whether the properties of the connecting point 112 correspond to the ideal state.

A transport device 130, which moves the containers 111 from one inspection station to the next in succession, is provided for supplying containers to the inspection stations which are disposed, one after the other, in succession. As shown more clearly in FIG. 13, the transport device 130 has a carrier 136, in the form of a bar, as the actual transport element extending above the inspection stations 101 to 105 and 107 along the inspection zone (see FIG. 12). For the ampoules or containers 111 to be transported, the carrier 136 has receptacles 138 at the bottom, disposed at intervals from one another, corresponding to the intervals between the inspection stations along the inspection zone. The receptacles 138 have vacuum holders, which can be controlled via suction lines 140, for holding ampoules 111 on the respective receptacle 138 and for releasing the respective ampoule 111. The carrier 136 can be moved back and forth, and up and down, along the inspection zone, according to the principle of cycled feed, for its function as a conveyor, as indicated with the double arrows 188 in FIG. 13. The carrier 136 with the outermost receptacle 138 at the left in FIG. 13 picks up an ampoule 111 from the separation device 114 at the inspection station 101 and delivers it to the next inspection station 102 in the following transport step. At the same time, an ampoule 111 is removed from this inspection station by the receptacle 138, which is connected at the right and transfers this ampoule, in turn, to the following inspection station 103 and so forth. For these movement steps, the transport device 130 has a drive device 192, whose geared motor 194 moves a carriage 190 along a guide rail 196, horizontally and vertically, together with the guide rail 196, by a crank drive concealed in FIGS. 12 and 13 and therefore not visible. The carrier 136 is connected to the carriage 190 and then executes the combined transport movements, while the holding devices on the receptacle 138 are controlled via the suction lines 140 for pickup and release of the ampoules.

Figure 16:
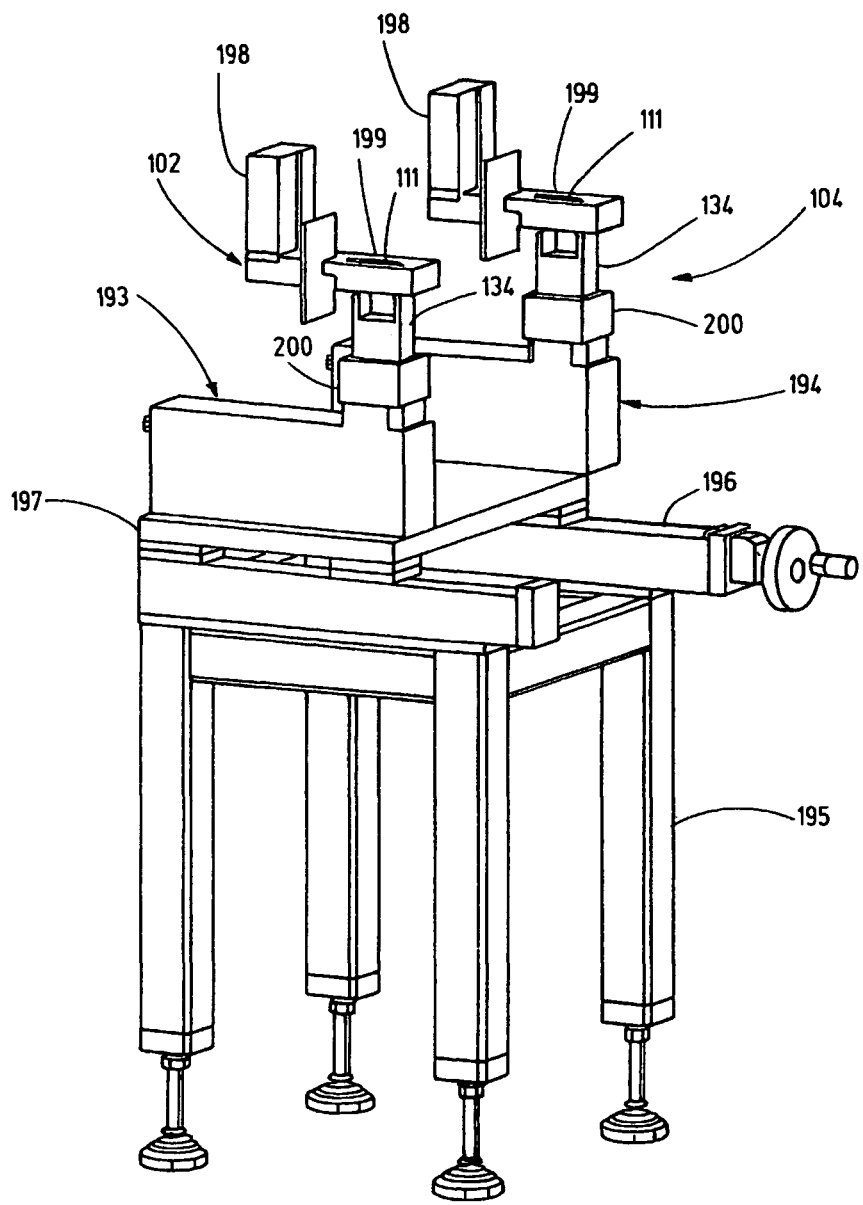
FIG. 16 is an enlarged, perspective view of the second and fourth inspection stations according to the second exemplary embodiment of the invention.
Figure 17:
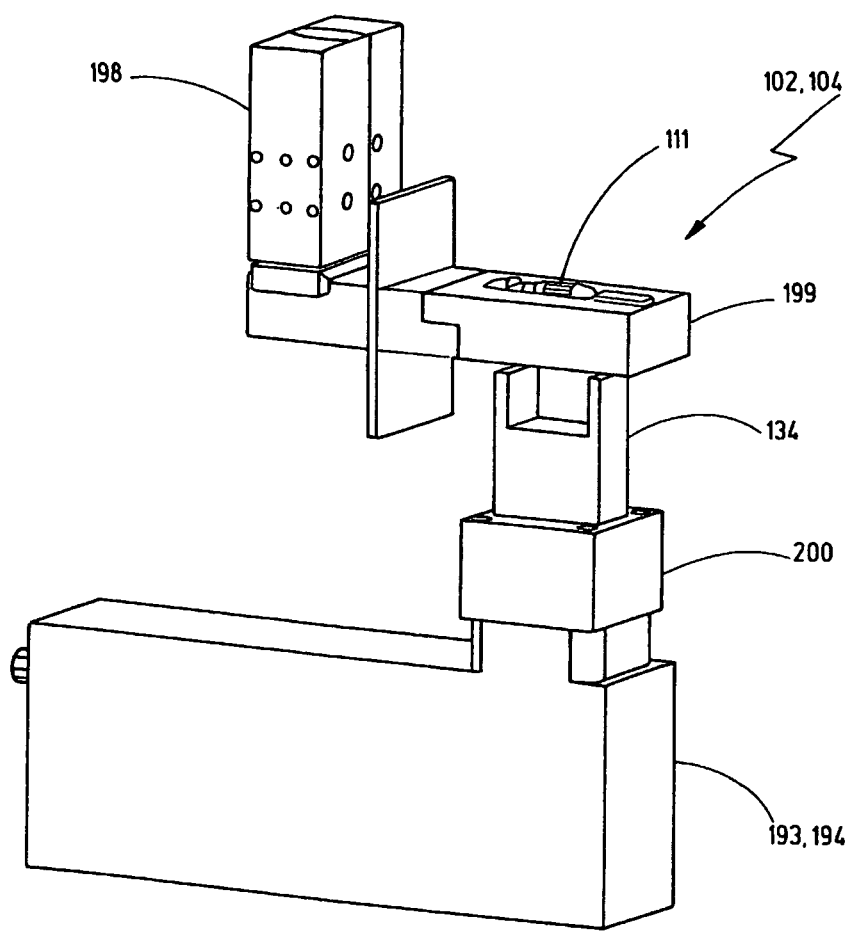
FIG. 17 is a further enlarged perspective oblique view of a part of the weighing stand of the second and/or fourth inspection stations according to the second exemplary embodiment of the invention.

After the twist-off torque, in separating the container 111 from the container strip 109, is detected in the first inspection station 101, the container 111 is conveyed to the inspection station 102 by the transport device 130. This station is a weighing station for automatic determination of the total weight of the container 111 filled with container contents. FIGS. 16 and 17 show details of the weighing stand. As can be seen in particular in FIG. 16, the weighing stands 193, 194 of the inspection stations 102 and 104 are disposed on their own frame 195, independently of the other inspection stations, to increase measurement precision by eliminating interfering influences from the other inspection stations. A plate 197, which is displaceable in a downward direction by a carriage 196, is disposed on the frame 195 and has two weighing stands 193, 194, one weighing stand 193 weighing the full container product and the subsequent weighing stand 194 weighing the empty container 111. A container 111 placed in a holder 199 can be lowered vertically onto a U-shaped weighing element 134 by a lowering device 198 at each inspection station 102, 104. A spacer 200 is provided between the weighing element 134 and the weighing stand 193, 194. Once the container 111 has been placed on the weighing stand 193, 194, it is decoupled from the holder 199 that can be allocated to it, so that the holder, with its own weight, cannot falsify the measurement result.

After detecting the weight, the weighed container 111, which is still filled, goes to inspection station 103, which has its own device for emptying the container contents. The important details of the emptying device can be seen in FIG. 18. To empty the container contents, a vent opening is formed by a puncturing needle 143, which can be moved in the downward direction and vertically on the neck part 139, while a cannula 145 forms an emptying opening on the bottom part of the main part 141 of the container. The cannula also is movable vertically and in the downward direction. The cannula 145 has a suction connection 147 to empty the container 111 by suction. The puncturing needle 143 and the cannula 145 are therefore mounted on holders 201, 202 which are attached to carriages 203, 204. Carriages 203, 204 are adjustable in their position, independently of one another, by hand wheels 205, 206. Position readings 207, 208 facilitate and accelerate the required adjustment operations. During emptying, the container 111 is held in a receptacle 209 between a holder 210 and a closable cover 211.

Figure 18:
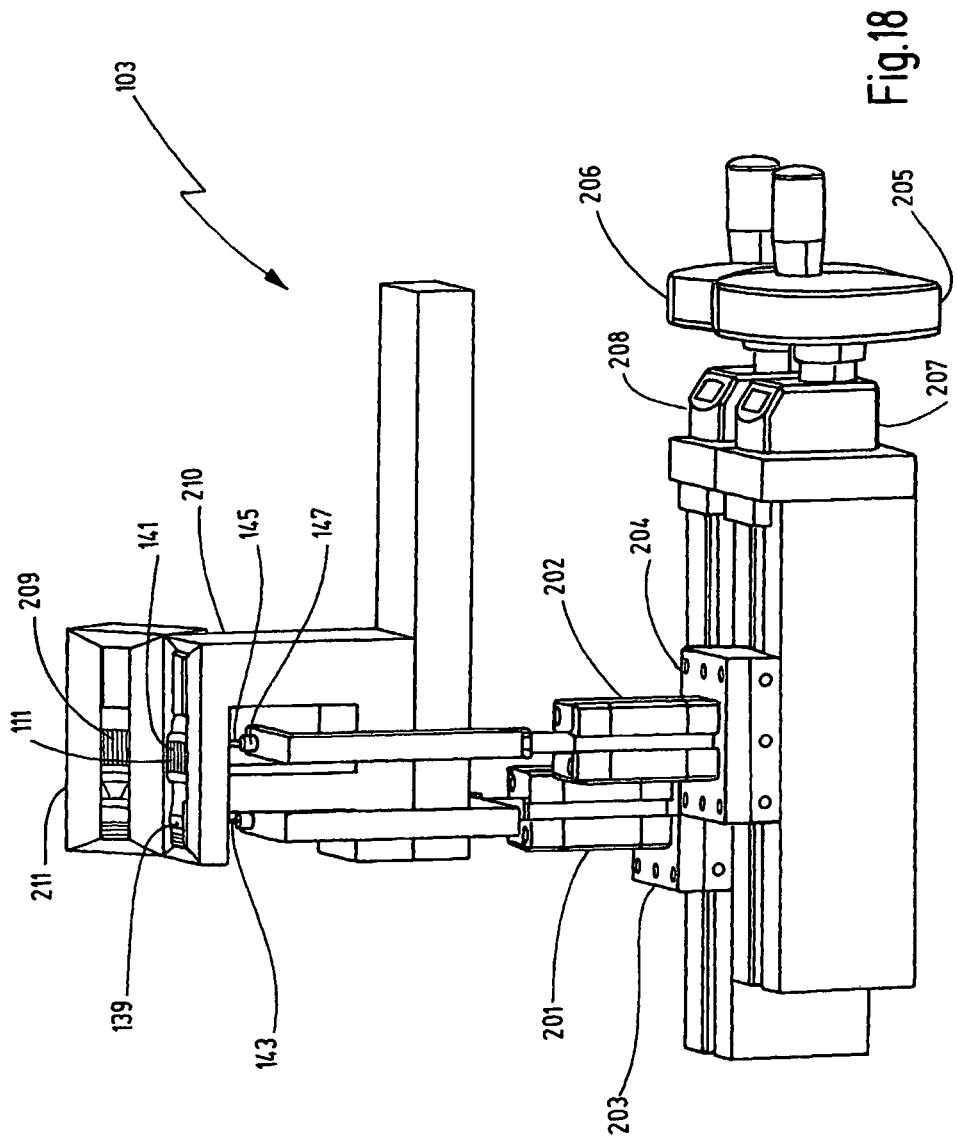
FIG. 18 is a highly simplified and schematic perspective view, enlarged in comparison with FIGS. 1 and 2, of a third inspection station having an emptying device according to the second embodiment of the invention.

In the next transport step of the transport device 130, the empty container 111 moves from the inspection station 103 to the inspection station 104, which is the second weighing station, corresponding in design and function to the inspection station already described with reference to FIGS. 17 and 18, except that now the tare weight of the previously emptied container 111 is detected. Thus, the mass of the preferably liquid container contents is ascertained precisely as the test result by comparing the total weight with the tare weight.

The next inspection station 105 (see FIG. 19) has a twist-off device 153 which removes an end part that is integrally molded on the neck part 139 of the container 111, in the form of a twist toggle 151, by twisting it off the container 111 as the torque required for this twist off is detected. The twist-off device 153 therefore has a twist-off unit, which is displaceable on a carriage 155 for this purpose, and drives a controllable locking pliers 163 by a rotary drive 157 via a safety coupling 159 and a torque sensor 161. This locking pliers grips and securely clamps the toggle 151 by displacement of the carriage 155, so that the toggle can be twisted off by the drive 157. The twist-off torque detected thereby signals whether the connection of the toggle 151 to the container 111 corresponds to the target state.

In the next step, the container 111 moves to the inspection station 107 (see FIG. 20), which has an optical measuring device 173 for detecting the wall thickness of the container walls 177. The measuring device 173 therefore has a movable laser measuring sensor 179, which can be moved into a suitable position on a carriage 226 with a hand wheel 227. To permit accurate positioning, a position sensor 228 is assigned to the carriage 226. The measuring sensor 179 is designed so that it can measure the thickness of opposing container walls 177 in one step. The container may therefore be gripped and rotated by a gripping device 229, which is disposed in such a way as to be movable on a carriage 230. The gripping device 229 comprises a servo motor 231 and a gripper 233, which has gripping fingers 234 and is rotatably mounted on a bearing block 232. By the laser measurement, any sawing that is still necessary in the first exemplary embodiment, or some other form of opening of the container 111, may be omitted.

After detecting the actual value for the wall thickness in the inspection station 107, the container 111 then moves to the ejection station 108 (see FIG. 12), which ejects the finished and inspected container 111 into a product collector 183.

Based on the modular design of the components for the inspection devices, the retaining inserts for the container products or ampoule products may be varied in a wide range of applications, so that a wide variety of types of products can be inspected for specified properties, using only one inspection device. Thus, containers or ampoule products having cylindrical, oval or polygonal cross-sectional shapes can be inspected with one inspection device with an appropriate adjustment of the receptacle modules. Individual ampoules or individual containers can also be inspected in just the same way as containers or ampoule products joined in a strip. Inspections will not be performed on the entire production output of one manufacturing machine, but will only be performed on a statistically relevant random sample from ongoing production selected for inspection. In addition, a wide variety of driving systems may also be used for activation of the inspection stations. In addition to hydraulic and pneumatic drives, electric drives, such as stepping motors and the like, may also be used.

The greatest advantage of the automatic inspection is that the inspection values thus obtained can be duplicated and are not subject to any subjective evaluation by inspection personnel. The test values, obtained automatically in this respect, are suitable for providing reliable information about the adjustment parameters of the upstream manufacturing machine in the sequence. Thus, for example, if the wall thickness is too small, more plastic material may be introduced into the shaping machine. If the quality of the plastic proves to be inferior, then the plastic material to be supplied can be changed and in particular a different blend of plastic material may be used. If the container or ampoule filling quantity is not correct, then the feed to the manufacturing machine can be controlled automatically. In particular, through long-term monitoring of the test results, wear on the manufacturing machine can be ascertained, so that parts of the machine can be replaced upon reaching a preselectable wear level. For example, worn manufacturing molds may be replaced by new molds. A suitable machine control, along with memory programming, supports the adjustment processes between the test device and the respective manufacturing machine in this regard.

While various embodiments have been chosen to illustrate the invention, it will be understood by those skilled in the art that various changes and modifications can be made therein without departing from the scope of the invention as defined in the claims.

The invention claimed is:

1. A device for establishing presence of specified characteristics of a container, comprising:
   a container product including a container strip with containers made of plastic and filled with container contents, the containers being joined together separably at connection points;
   a test device receiving the container product;
   a first inspection station of the test device having a separator for machine separation of the containers from the container strip by a mechanical twist-off, the separator including a holder partially surrounding and gripping one of the containers to be separated and a rotary drive coupled to the holder to rotate the holder with the one of the containers gripped in the holder to twist off the one of the containers from the container strip; and
   a torque sensor coupled to the rotary drive detecting a torque required to twist off the one of the containers.

2. A device according to claim 1 wherein
   the test device comprises a transport with container receptacles for movement from the first inspection station to additional inspection stations disposed along an inspection zone of the test device.

3. A device according to claim 2 wherein
   the transport comprises a motor-driven carousel that moves the container receptacles along a circular inspection path to the additional inspection stations disposed along the inspection path.

4. A device according to claim 3 wherein
   the test device comprises an ejection station that ejects one of the containers from the respective container receptacle of the transport, the ejection station being on the circular inspection path in front of the first inspection station.

5. A device according to claim 2 wherein
   each of the receptacles comprises a bearing part receiving the respective container and a cover part movable relative to the bearing part between a closed position surrounding a partial region of the respective container supported in the respective receptacle and an open position raised from the respective bearing part; and
   the transport comprises a control engageable with said cover parts to move the cover parts into the closed and open positions.

6. A device according to claim 2 wherein
   the inspection stations are disposed along an inspection path in a longitudinal direction; and
   the transport comprises transport elements moving the containers in succession from one of the inspection stations to a next one of the inspection stations.

7. A device according to claim 6 wherein
   the transport element comprises a carrier movable back and forth and movable up and down along and relative to the inspection path;
   the container receptacles are disposed on the carrier at intervals corresponding to intervals between the inspection stations; and
   the container receptacles have container holding and releasing devices that pick up the containers at one of the inspection stations and release the containers at a subsequent one of the inspection stations.

8. A device according to claim 1 wherein
the test device comprises a second inspection having a weighing stand automatically detecting weight of the containers filled with container contents.

9. A device according to claim 8 wherein
the test device comprises a third inspection station having a device emptying the container contents of the containers.

10. A device according to claim 9 wherein
the test device comprises a fourth inspection station having a weight stand automatically determining weights of the containers after being emptied of the container contents.

11. A device according to claim 10 wherein
each of the containers comprises a main part and end part at a removal area on a neck part with the end part being removable by a twisting motion from the end part; and
at the test device comprises a fifth inspection station having a twist-off device with a rotary drive and with a torque sensor detecting a torque required to remove the end parts from the containers.

12. A device according to claim 10 wherein
the test device comprises an incision station having a cutter forming incisions in the containers and exposing cross sections of wall parts of the containers.

13. A device according to claim 12 wherein
the test device comprises a wall thickness measuring station having a wall thickness measuring station automatically detecting wall thicknesses of the containers that have been cut.

14. A device according to claim 10 wherein
said test drive comprises a wall thickness measuring station having a nondestructive wall thickness detector measuring wall thicknesses of the containers, the wall thickness detector being at least one of an ultrasound detector or an optical detector.

15. A method for establishing the presence of specified characteristics of a container, comprising the steps of:
providing a container product to a testing device, the container product including a container strip with containers made of plastic and filled with container contents, the containers being separably joined together at connection points;
separating the containers automatically from the container strip by twisting by machine and automatically measuring a torque separation force required for the separating in a first inspection station and then comparing the torque separation force measured with a target torque separation force value;
automatically transferring the containers filled with the container contents by machine after the separating to a second inspection station and automatically weighing the separated containers to determine a total weight of each separated container in the second inspection station, and then comparing the total weight measured with a target total weight;
automatically transferring the containers after the separating and weighing to a third inspection station by machine and automatically emptying the container contents from the containers in the third inspection station to provide emptied containers; and
automatically transferring the emptied containers by machine to a fourth inspection station and automatically weighing the emptied containers in the fourth inspection station to measure the tare weight thereof, and automatically comparing the tare weight measured and the total weight measured to ascertain a measured weight of the container content and then comparing the measured weight of the container contents with a target weight of container contents.

16. A method according to claim 15 wherein
each container is provided with a main part and an end part at a removal area on a neck part, with the end part being removable by a twisting motion from the main part; and
the containers are automatically transferred from the fourth inspection station to a fifth inspection station by machine where each end part of each container is automatically twisted off mechanically and where a twist torque required for twisting off of the end part mechanically is measured, the twist torque measured being compared to a target twisted torque.

17. A method according to claim 15 wherein
the containers are automatically transferred to an incision inspection station by machine where incisions are made in the containers exposing portions of container walls of the containers to provide cut containers.

18. A method according to claim 17 wherein
the cut containers are automatically brought by machine to a thickness inspection station where a wall thickness of a container wall of each container is automatically measured and where each wall thickness measured is compared to a target wall thickness.

19. A method according to claim 18 wherein
each container is automatically transferred by machine to an ejection station after each wall thickness is measured and is discharged from the testing device at the ejection station.

20. A method according to claim 15 wherein
the containers are automatically brought by machine to a thickness inspection station where container wall thickness is measured in a nondestructive manner on at least one location of each of the containers by at least one of an ultrasound measurement or an optical measurement.

21. A method according to claim 15 wherein
measured values in the inspection stations are detected and stored for obtaining statistical analysis of deviations of the measured values relative to respective target values by electronic acquisition, storage and evaluation media.

22. A method according to claim 21 wherein
the deviations of the measured values relative to the respective target values are forwarded to a machine control of a container manufacturing device to optimize manufacturing parameters such that the deviations in the measured and target values approaches zero.

* * * * *